United States Patent
Edwards et al.

(10) Patent No.: US 6,569,159 B1
(45) Date of Patent: *May 27, 2003

(54) CELL NECROSIS APPARATUS

(75) Inventors: Stuart D. Edwards, Los Altos, CA (US); James Baker, Palo Alto, CA (US); Hugh Sharkey, Redwood Shores, CA (US); Ronald G. Lax, Grass Valley, CA (US)

(73) Assignee: Rita Medical Systems, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/513,727

(22) Filed: Feb. 24, 2000

Related U.S. Application Data

(63) Continuation-in-part of application No. 09/383,166, filed on Aug. 25, 1999, now Pat. No. 6,471,698, which is a continuation of application No. 08/802,195, filed on Feb. 14, 1997, now Pat. No. 6,071,280, which is a continuation-in-part of application No. 08/515,379, filed on Aug. 15, 1995, now Pat. No. 5,683,384, which is a continuation-in-part of application No. 08/290,031, filed on Aug. 12, 1994, now Pat. No. 5,536,267, which is a continuation-in-part of application No. 08/148,439, filed on Nov. 8, 1993, now Pat. No. 5,458,597, application No. 09/513,727, which is a continuation-in-part of application No. 09/364,203, filed on Jul. 30, 1999, which is a continuation of application No. 08/623,652, filed on Mar. 29, 1996, now Pat. No. 5,935,123, which is a division of application No. 08/295,166, filed on Aug. 24, 1994, now Pat. No. 5,599,345, which is a continuation-in-part of application No. 08/148,439, filed on Nov. 8, 1993, now Pat. No. 5,458,597.

(51) Int. Cl.$^7$ .............................................. A61B 18/18
(52) U.S. Cl. ......................................... 606/41; 607/101
(58) Field of Search ............................ 606/41, 42, 45, 606/50; 607/101–105

(56) References Cited

U.S. PATENT DOCUMENTS

| | | |
|---|---|---|
| 5,122,137 A | 6/1992 | Lennox |
| 5,122,138 A | 6/1992 | Manwaring |
| 5,165,421 A | 11/1992 | Fleischhacker |
| 5,246,014 A | 9/1993 | Williams |
| 5,281,218 A | 1/1994 | Imran |
| 5,314,466 A | 5/1994 | Stern et al. |
| 5,322,503 A | 6/1994 | Desai |
| 5,328,467 A | 7/1994 | Edwards et al. |

(List continued on next page.)

FOREIGN PATENT DOCUMENTS

| | | |
|---|---|---|
| BE | PCT/BE99/00106 | 2/2000 |
| BE | PCT/BE99/00107 | 2/2000 |
| DE | 21 24 684 A2 | 11/1972 |

*Primary Examiner*—Michael Peffley
(74) *Attorney, Agent, or Firm*—Jacqueline F. Mahoney; Peter J. Dehlinger; Perkins Coie LLP

(57) ABSTRACT

A cell necrosis apparatus comprises an elongated delivery device including a lumen and an energy delivery device. The energy delivery device includes at least a first and a second RF electrode each with a tissue piercing distal portion. The first and second RF electrodes are positionable in the elongated delivery device in a compacted state and deployable from the elongated delivery device with curvature in a deployed state. The first and second RF electrodes exhibit a changing direction of travel when advanced from the elongated delivery device to a selected tissue site. At least one infusion port is coupled to one of the elongated delivery device, the energy delivery device, the first RF electrode or the second RF electrode.

16 Claims, 31 Drawing Sheets

U.S. PATENT DOCUMENTS

| | | | |
|---|---|---|---|
| 5,334,193 A | * 8/1994 | Nardella | 607/101 |
| 5,334,206 A | 8/1994 | Daikuzono | |
| 5,336,178 A | 8/1994 | Kaplan et al. | |
| 5,336,222 A | 8/1994 | Durgin, Jr. et al. | |
| 5,342,357 A | 8/1994 | Nardella | |
| 5,370,675 A | * 12/1994 | Edwards et al. | 607/101 |
| 5,383,876 A | 1/1995 | Nardella | |
| 5,403,311 A | 4/1995 | Abele | |
| 5,431,649 A | 7/1995 | Mulier et al. | |
| 5,433,708 A | 7/1995 | Nichols et al. | |
| 5,437,660 A | 8/1995 | Johnson et al. | |
| 5,437,662 A | 8/1995 | Nardella | |
| 5,454,807 A | 10/1995 | Lennox et al. | |
| 5,514,130 A | * 5/1996 | Baker | 606/41 |
| 5,536,267 A | 7/1996 | Edwards et al. | |
| 5,551,426 A | 9/1996 | Hummel et al. | |
| 5,556,377 A | 9/1996 | Rosen et al. | |
| 5,558,672 A | 9/1996 | Edwards et al. | |
| 5,558,673 A | 9/1996 | Edwards et al. | |
| 5,560,358 A | 10/1996 | Arnold et al. | |
| 5,562,703 A | 10/1996 | Desai | |
| 5,599,345 A | 2/1997 | Edwards et al. | |
| 5,599,346 A | 2/1997 | Edwards et al. | |
| 5,605,539 A | 2/1997 | Buelna et al. | |
| 5,609,151 A | 3/1997 | Mulier et al. | |
| 5,620,481 A | 4/1997 | Desai et al. | |
| 5,697,909 A | 12/1997 | Eggers et al. | |
| 5,725,524 A | 3/1998 | Mulier et al. | |
| 5,735,811 A | 4/1998 | Brisken | |
| 5,800,482 A | 9/1998 | Pomeranz et al. | |
| 5,807,395 A | 9/1998 | Mulier et al. | |
| 5,827,276 A | * 10/1998 | LeVeen et al. | 606/41 |
| 5,855,576 A | 1/1999 | Leveen et al. | |
| 5,868,740 A | 2/1999 | Leveen et al. | |
| 5,876,398 A | 3/1999 | Mulier et al. | |
| 5,879,349 A | 3/1999 | Edwards | |
| 5,888,198 A | 3/1999 | Eggers et al. | |
| 5,891,095 A | 4/1999 | Eggers et al. | |
| 5,897,553 A | 4/1999 | Mulier et al. | |
| 5,902,328 A | 5/1999 | Lafontaine | |
| 5,906,613 A | 5/1999 | Mulier et al. | |
| 5,913,854 A | 6/1999 | Maguire et al. | |
| 5,913,856 A | 6/1999 | Chia et al. | |
| 5,971,968 A | 10/1999 | Tu et al. | |
| 5,997,532 A | 12/1999 | McLaughlin et al. | |
| 6,013,074 A | 1/2000 | Taylor | |
| 6,015,407 A | 1/2000 | Rieb et al. | |
| 6,016,809 A | 1/2000 | Mulier et al. | |
| 6,024,739 A | 2/2000 | Ponzi et al. | |
| 6,030,379 A | 2/2000 | Panescu et al. | |
| 6,032,077 A | 2/2000 | Pomeranz | |
| 6,056,747 A | 5/2000 | Saadat et al. | |
| 6,063,081 A | 5/2000 | Mulier et al. | |
| 6,086,585 A | 7/2000 | Hovda et al. | |
| 6,129,726 A | 10/2000 | Edwards et al. | |
| 6,131,577 A | 10/2000 | Nicholson | |
| 6,238,393 B1 | 5/2001 | Mulier et al. | |

* cited by examiner

CELL NECROSIS APPARATUS

CROSS-REFERENCE TO RELATED APPLICATIONS

This application is a continuation-in-part of U.S. Ser. No. 09/383,166 filed Aug. 25, 1999 now U.S. Pat. No. 6,471,698 which is a continuation of U.S. Ser. No. 08/802,195, filed Feb. 14, 1997, now U.S. Pat. No. 6,071,280, which is a continuation-in-part of application Ser. No. 08/515,379, filed Aug. 15, 1995, now U.S. Pat. No. 5,683,384 which is a continuation-in-part of U.S. patent application Ser. No. 08/290,031, filed Aug. 12, 1994, now U.S. Pat. No. 5,536,267 which is a continuation-in-part of U.S. patent application Ser. No. 08/148,439, filed Nov. 8, 1993, now U.S. Pat. No. 5,458,597, each of which is incorporated by reference herein. This application is also a continuation-in-part of application Ser. No. 09/364,203, filed Jul. 30, 1999, which is a continuation of application Ser. No. 08/623,652, filed Mar. 29, 1996, now U.S. Pat. No. 5,935,123, which is a divisional of application Ser. No. 08/295,166, filed Aug. 24, 1994, now U.S. Pat. No. 5,599,345, which is a continuation-in-part of application Ser. No. 08/148,439, filed Nov. 8, 1993, now U.S. Pat. No. 5,458,597, each of which is incorporated by reference herein.

BACKGROUND OF THE INVENTION

1. Field of the Invention

This invention relates generally to an apparatus for the treatment and ablation of body masses, such as tumors, and more particularly, to an RF treatment system suitable for multi-modality treatment with an infusion delivery and a retractable multiple needle electrode apparatus that surrounds an exterior of a tumor with a plurality of needle electrodes and defines an ablative volume. The system maintains a selected power at an electrode that is independent of changes in current or voltage.

2. Description of Related Art

Current open procedures for treatment of tumors are extremely disruptive and cause a great deal of damage to healthy tissue. During the surgical procedure, the physician must exercise care in not cutting the tumor in a manner that creates seeding of the tumor, resulting in metastasis. In recent years development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysosomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the body. Certain techniques have been developed with microwave radiation and ultrasound to focus energy at various desired depths. RF applications may be used at depth during surgery. However, the extent of localization is generally poor, with the result that healthy tissue may be harmed. Induction heating gives rise to poor localization of the incident energy as well. Although induction heating may be achieved by placing an antenna on the surface of the body, superficial eddy currents are generated in the immediate vicinity of the antenna. When it is driven using RF current unwanted surface heating occurs diminishing heating to the underlying tissue.

Thus, non-invasive procedures for providing heat to internal tumors have had difficulties in achieving substantial specific and selective treatment.

Hyperthermia, which can be produced from an RF or microwave source, applies heat to tissue but does not exceed 45 degrees C. so that normal cells survive. In thermotherapy, heat energy of greater than 45 degrees C. is applied, resulting in histological damage, desiccation and the denaturization of proteins. Hyperthermia has been applied more recently for therapy of malignant tumors. In hyperthermia, it is desirable to induce a state of hyperthermia that is localized by interstitial current heating to a specific area while concurrently insuring minimum thermal damage to healthy surrounding tissue. Often, the tumor is located subcutaneously and addressing the tumor requires either surgery, endoscopic procedures or external radiation. It is difficult to externally induce hyperthermia in deep body tissue because current density is diluted due to its absorption by healthy tissue. Additionally, a portion of the RF energy is reflected at the muscle/fat and bone interfaces which adds to the problem of depositing a known quantity of energy directly on a small tumor.

Attempts to use interstitial local hyperthermia have not proven to be very successful. Results have often produced nonuniform temperatures throughout the tumor. It is believed that tumor mass reduction by hyperthermia is related the thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure more effective treatment.

The same is true for ablation of the tumor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

There have been a number of different treatment methods and devices for minimally invasively treating tumors. One such example is an endoscope that produces RF hyperthermia in tumors, as disclosed in U.S. Pat. No. 4,920,978. A microwave endoscope device is described in U.S. Pat. No. 4,409,993. In U.S. Pat. No. 4,920,978, an endoscope for RF hyperthermia is disclosed.

In U.S. Pat. No. 4,763,671, a minimally invasive procedure utilizes two catheters that are inserted interstitially into the tumor. The catheters are placed within the tumor volume and each is connect to a high frequency power source.

In U.S. Pat. No. 4,565,200, an electrode system is described in which a single entrance tract cannula is used to introduce an electrode into a selected body site.

However, as an effective treatment device, electrodes must be properly positioned relative to the tumor. After the electrodes are positioned, it is then desirable to have controlled application and deposition of RF energy to ablate the tumor. This reduces destruction of healthy tissue. There is a need for a RF tumor treatment apparatus that is useful for minimally invasive procedures. It would be desirable for such a device to surround the exterior of the tumor with treatment electrodes, defining a controlled ablation volume, and subsequently the electrodes deliver a controlled amount of RF energy. Additionally, there is a need for a device with infusion capabilities during a pre-ablation step, and after ablation the surrounding tissue can be preconditioned with electromagnetic ("EM") energy at hyperthermia temperatures less than 45 degrees. This would provide for the synergistic affects of chemotherapy and the instillation of a variety of fluids at the tumor site after local ablation and hyperthermia.

SUMMARY OF THE INVENTION

In an embodiment of the invention, a cell necrosis apparatus comprises an elongated delivery device including a lumen and an energy delivery device. The energy delivery device includes at least a first and a second RF electrode each with a tissue piercing distal portion. The first and second RF electrodes are positionable in the elongated delivery device in a compacted state and deployable from the elongated delivery device with curvature in a deployed state. The first and second RF electrodes exhibit a changing direction of travel when advanced from the elongated delivery device to a selected tissue site. At least one infusion port is coupled to one of the elongated delivery device, the energy delivery device, the first RF electrode or the second RF electrode. The apparatus may be configured such that the first and second RF electrodes have independent fluid delivery.

In another embodiment, a tissue ablation apparatus includes a delivery catheter, with distal and proximal ends. A handle is attached to the proximal end of the delivery catheter. An electrode deployment apparatus is positioned at least partially in the delivery catheter. It includes a plurality of electrodes that are retractable in and out of the catheter's distal end. The electrodes are in a non-deployed state when they are positioned within the delivery catheter. As they are advanced out the distal end of the catheter they become deployed, and define an ablation volume. Each electrode has a first section with a first radius of curvature, and a second section, extending beyond the first section, having a second radius of curvature or a substantially linear geometry. Alternatively, each deployed electrode has at least two radii of curvature that are formed when the needle is advanced through the delivery catheter's distal end and becomes positioned at a selected tissue site. Also each deployed electrode can have at least one radius of curvature in two or more planes. Further, the electrode deployment apparatus can include at least one deployed electrode having at least radii of curvature, and at least one deployed electrode with at least one radius of curvature in two or more planes.

In a further embodiment, the electrode deployment apparatus has at least one deployed electrode with at least one curved section that is located near the distal end of the delivery catheter, and a non-curved section which extends beyond the curved section of the deployed electrode. The electrode deployment apparatus also has at least one deployed electrode with at least two radii of curvature.

In another embodiment of the invention, each deployed electrode has at least one curved section located near the distal end of the delivery catheter, and a non-curved section that extends beyond the curved section of the deployed electrode.

An electrode template can be positioned at the distal end of the delivery catheter. It assists in guiding the deployment of the electrodes to a surrounding relationship at an exterior of a selected mass in a tissue. The electrodes can be hollow. An adjustable electrode insulator can be positioned in an adjacent, surrounding relationship to all or some of the electrodes. The electrode insulator is adjustable, and capable of being advanced and retracted along the electrodes in order to define an electrode conductive surface.

The electrode deployment apparatus can include a cam which advances and retracts the electrodes in and out of the delivery catheter's distal end. Optionally included in the delivery catheter are one or more guide tubes associated with one or more electrodes. The guide tubes are positioned at the delivery catheter's distal end.

Sources of infusing mediums, including but not limited to electrolytic and chemotherapeutic solutions, can be associated with the hollow electrodes. Electrodes can have sharpened, tapered ends in order to assist their introduction through tissue, and advancement to the selected tissue site.

The electrode deployment apparatus is removable from the delivery catheter. An obturator is initially positioned within the delivery catheter. It can have a sharpened distal end. The delivery catheter can be advanced percutaneously to an internal body organ, or site, with the obturator positioned in the delivery catheter. Once positioned, the obturator is removed, and the electrode deployment apparatus is inserted into the delivery catheter. The electrodes are in non-deployed states, and preferably compacted or spring-loaded, while positioned within the delivery catheter. They are made of a material with sufficient strength so that as the electrodes emerge from the delivery catheter's distal end they are deployed three dimensionally, in a lateral direction away from the periphery of the delivery catheter's distal end. The electrodes continue their lateral movement until the force applied by the tissue causes the needles to change their direction of travel.

Each electrode now has either, (i) a first section with a first radius of curvature, and a second section, extending beyond the first section, having a second radius of curvature or a substantially linear section, (ii) two radii of curvature, (iii) one radius of curvature in two or more planes, or (iv) a combination of two radii of curvature with one of them in two or more planes. Additionally, the electrode deployment apparatus can include one or more of these deployed geometries for the different electrodes in the plurality. It is not necessary that every electrode have the same deployed geometry.

After the electrodes are positioned around a mass, such as a tumor, a variety of solutions, including but not limited to electrolytic fluids, can be introduced through the electrodes to the mass in a pre-ablation step. RF energy is applied, and the mass is desiccated. In a post-ablation procedure, a chemotherapeutic agent can then be introduced to the site, and the electrodes are then retracted back into the introducing catheter. The entire ablative apparatus can be removed, or additional ablative treatments be conducted.

DETAILED DESCRIPTION

Figure 1:
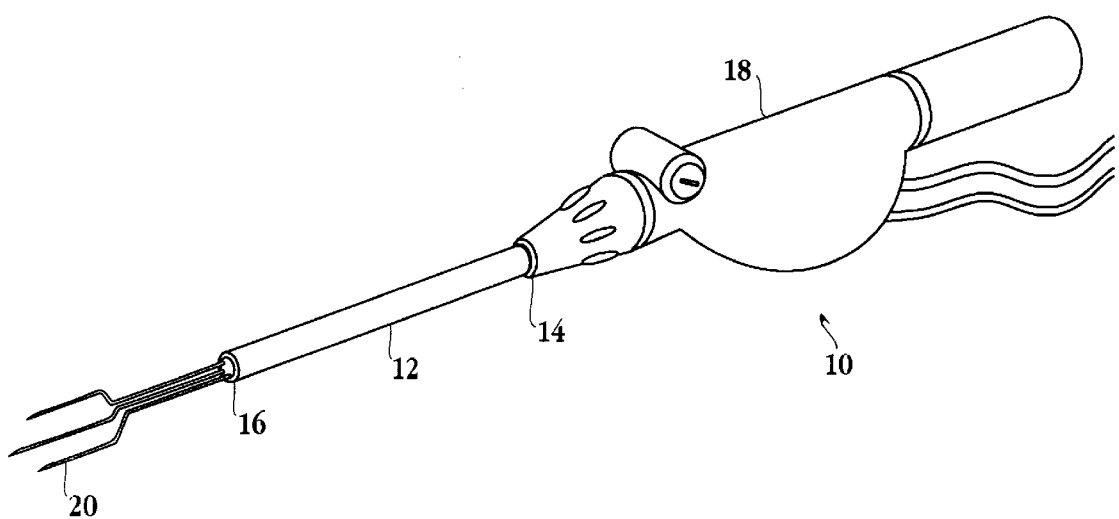
FIG. 1 is a perspective view of the tissue ablation apparatus of the invention, including a delivery catheter, handle, and deployed electrodes.

A tissue ablation apparatus 10 of the invention is illustrated in FIG. 1. Ablation apparatus 10 includes a delivery catheter 12, well known to those skilled in the art, with a proximal end 14 and a distal end 16. Delivery catheter 12 can be of the size of about 5 to 16 F. A handle 18 is removably attached to proximal end 14. An electrode deployment device is at least partially positioned within delivery catheter 12, and includes a plurality of electrodes 20 that are retractable in and out of distal end 16. Electrodes 20 can be of different sizes, shapes and configurations. In one embodiment, they are needle electrodes, with sizes in the range of 27 to 14 gauge. Electrodes 20 are in non-deployed positions while retained in delivery catheter. In the non-deployed positions, electrodes 20 may be in a compacted state, spring loaded, generally confined or substantially straight if made of a suitable memory metal such as nitinol. As electrodes 20 are advanced out of distal end 16 they become distended in a deployed state, which defines an ablative volume, from which tissue is ablated as illustrated more fully in FIG. 2. Electrodes 20 operate either in the bipolar or monopolar modes. When the electrodes are used in the bipolar mode, the ablative volume is substantially defined by the peripheries of the plurality of electrodes 20. In one embodiment, the cross-sectional width of the ablative volume is about 4 cm. However, it will be appreciated that different ablative volumes can be achieved with tissue ablation apparatus 10.

The ablative volume is first determined to define a mass, such as a tumor, to be ablated. Electrodes 20 are placed in a surrounding relationship to a mass or tumor in a predetermined pattern for volumetric ablation. An imaging system is used to first define the volume of the tumor or selected mass. Suitable imaging systems include but are not limited to, ultrasound, computerized tomography (CT) scanning, X-ray film, X-ray fluoroscopy, magnetic resonance imaging, electromagnetic imaging, and the like. The use of such devices to define a volume of a tissue mass or a tumor is well known to those skilled in the art.

With regard to the use of ultrasound, an ultrasound transducer transmits ultrasound energy into a region of interest in a patient's body. The ultrasound energy is reflected by different organs and different tissue types. Reflected energy is sensed by the transducer, and the resulting electrical signal is processed to provide an image of the region of interest. In this way, the ablation volume is then ascertained, and the appropriate electrode deployment device is inserted into delivery catheter 12.

The ablative volume is substantially defined before ablation apparatus 10 is introduced to an ablative treatment position. This assists in the appropriate positioning of ablation apparatus 10. In this manner, the volume of ablated tissue is reduced and substantially limited to a defined mass or tumor, including a certain area surrounding such a tumor, that is well controlled and defined. A small area around the tumor is ablated in order to ensure that all of the tumor is ablated.

Figure 2:
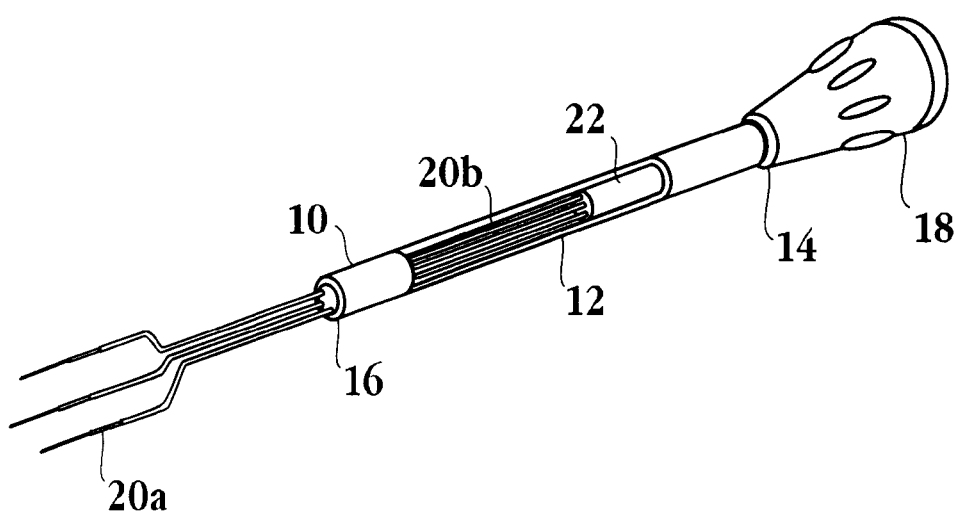
FIG. 2 is a cross-sectional view of the tissue ablation apparatus of the invention illustrated in FIG. 1.

With reference again to FIG. 2, electrode sections 20(*a*) are in deployed states when they are introduced out of distal end 16. Although electrodes 20 are generally in a non-distended configuration in the non-deployed state while positioned in delivery catheter 12, they can also be distended. Generally, electrode sections 20(*b*) are in retained positions while they are non-deployed. This is achieved by a variety of methods including but not limited to, (i) the electrodes are pre-sprung, confined in delivery catheter 12, and only become sprung (expanded) as they are released from delivery catheter 12, (ii) the electrodes are made of a memory metal, as explained in further detail below, (iii) the electrodes are made of a selectable electrode material which gives them an expanded shape outside of delivery catheter 12, or (iv) delivery catheter 12 includes guide tubes which serve to confine electrodes 12 within delivery catheter 12 and guide their direction of travel outside of the catheter to form the desired, expanded ablation volume. As shown in FIG. 2, electrodes 20 are pre-sprung while retained in delivery catheter 12. This is the non-deployed position. As they are advanced out of delivery catheter 12 and into tissue, electrodes 20 become deployed and begin to "fan" out from distal end 16, moving in a lateral direction relative to a longitudinal axis of delivery catheter 12. As deployed electrodes 20 continue their advancement, the area of the fan increases and extends beyond the diameter of distal end 16.

Significantly, each electrode 20 is distended in a deployed position, and collectively, the deployed electrodes 20 define a volume of tissue that will be ablated. As previously mentioned, when it is desired to ablate a tumor, either benign or malignant, it is preferable to ablate an area that is slightly in excess to that defined by the exterior surface of the tumor. This improves the chances that all of the tumor is eradicated.

Deployed electrodes 20 can have a variety of different deployed geometries including but not limited to, (i) a first section with a first radius of curvature, and a second section, extending beyond the first section, having a second radius of curvature or a substantially linear geometry, (ii) at least two radii of curvature, (iii) at least one radius of curvature in two or more planes, (iv) a curved section, with an elbow, that is located near distal end 16 of delivery catheter, and a non-curved section that extends beyond the curved section, or (v) a curved section near distal end 16, a first linear section, and then another curved section or a second linear section that is angled with regard to the first linear section. Deployed electrodes 20 need not be parallel with respect to each other. The plurality of deployed electrodes 20, which define a portion of the needle electrode deployment device, can all have the same deployed geometries, i.e., all with at least two radii of curvature, or a variety of geometries, i.e., one with two radii of curvature, a second one with one radius of curvature in two planes, and the rest a curved section near distal end 16 of delivery catheter 12 and a non-curved section beyond the curved section.

A cam 22, or other actuating device, can be positioned within delivery catheter and used to advance and retract electrodes 20 in and out of delivery catheter 12. The actual movement of cam can be controlled at handle 18. Suitable cams are of conventional design, well known to those skilled in the art.

Figure 3:
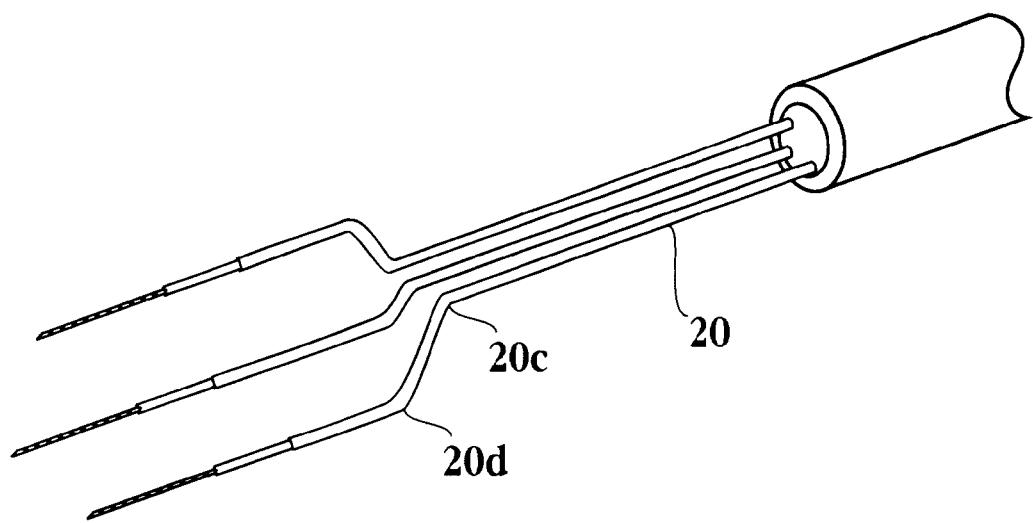
FIG. 3 is a perspective view of an electrode of the invention with two radii of curvature.
Figure 4:
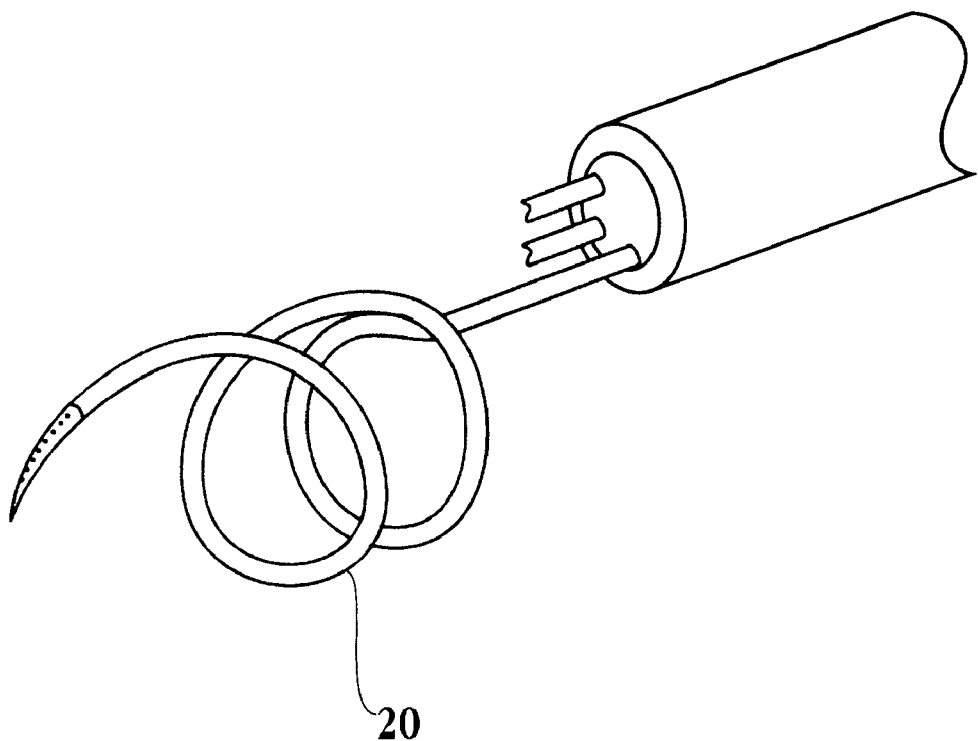
FIG. 4 is a perspective view of an electrode of the invention with one radius of curvature in three planes.
Figure 5:
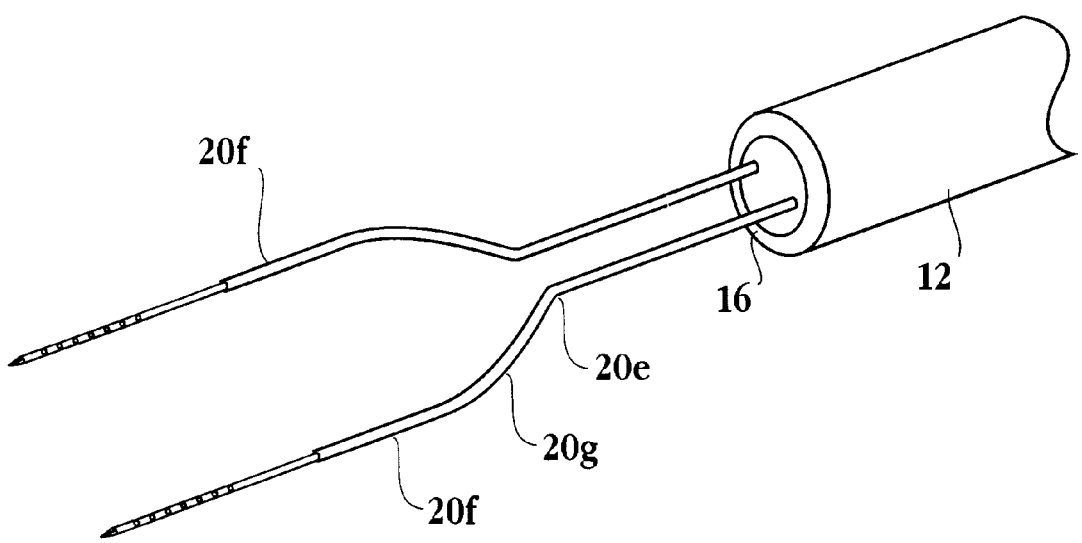
FIG. 5 is a perspective view of an electrode of the invention with one curved section, positioned close to the distal end of the delivery catheter, and a linear section.
Figure 6:
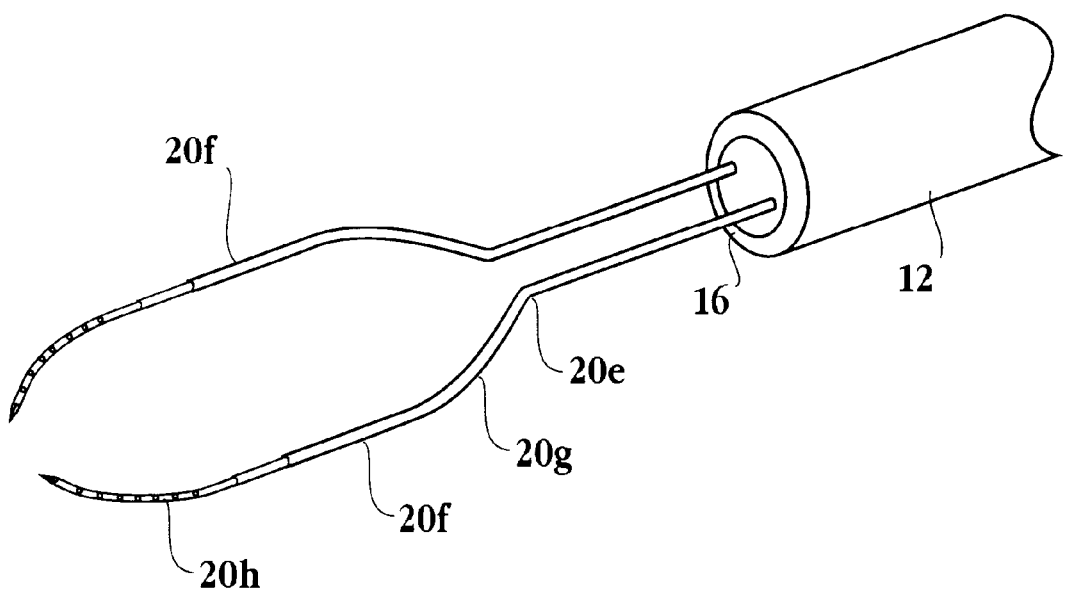
FIG. 6 is a perspective view of an electrode of the invention with one curved section, positioned close to the distal end of the delivery catheter, a generally first linear section, and then a second linear section that continues laterally with regard to the first linear section.

The different geometric configurations of electrodes 20 are illustrated in FIGS. 3 through 6. In FIG. 3, electrode 20 has a first radius of curvature 20(*c*) and a second radius of curvature 20(*d*). It can include more than two radii of curvature. As shown in FIG. 4, electrode 20 has at least one radius of curvature which extends to three planes. In FIG. 5, each electrode has a first curved section 20(*e*) which is near distal end 16 of delivery catheter 12. A first generally linear section 20(*f*) extends beyond curved section 20(*e*), and the two meet at an elbow 20(*g*). The electrodes 20 can serve as anodes and cathodes. The plurality of electrodes 20 can have linear sections 20(*f*) that are generally parallel to each other, or they can be non-parallel. FIG. 6 illustrates an electrode 20 that includes a first curved section 20(*e*) positioned near distal end 16 of delivery catheter 12, a first linear section 20(*f*), and a second linear section 20(*h*) which extends beyond first linear section 20(*f*). Section 20(*h*) can be linear, curved, or a combination of the two. The plurality of electrodes 20 illustrated in FIG. 6 can have parallel or non-parallel first linear sections 20(*f*).

In one embodiment of the invention, electrodes 20 are spring-loaded, and compacted in their non-deployed positions. As electrodes 20 are advanced out of distal end 16 of delivery catheter 12, they become deployed and fan out. Electrodes 20 continue this fanning out direction until the resistance of the tissue overcomes the strength of the material forming electrode 20. This causes electrode 20 to bend and move in a direction inward relative to its initial outward fanning direction. The bending creates curved sections 20(*c*) and 20(*d*) of FIG. 3, and can also result in the formation of the other electrode 20 geometries of FIGS. 4, 5 and 6. The extent of electrode 20 fan like travel is dependent on the strength of the material from which it is made. Suitable electrode materials include stainless steel, platinum, gold, silver, copper and other electromagnetic conducting materials including conductive polymers. Preferably, electrode 20 is made of stainless steel or nickel titanium and has dimensions of about 27 to 14 gauge.

In one embodiment, electrode 20 is made of a memory metal, such as nickel titanium, commercially available from Raychem Corporation, Menlo Park, Calif. Additionally, a resistive heating element can be positioned in an interior lumen of electrode 20. Resistive heating element can be made of a suitable metal that transfers heat to electrode 20, causing deployed electrode 20 to become deflected when the temperature of electrode 20 reaches a level that causes the electrode material, such as a memory metal, to deflect, as is well known in the art. Not all of electrode 20 need be made of a memory metal. It is possible that only that distal end portion of electrode 20, which is introduced into tissue, be made of the memory metal in order to effect the desired deployed geometrical configuration. Additionally, mechanical devices, including but not limited to steering wires, can be attached to the distal end of electrode 20 to cause it to become directed, deflected and move about in a desired direction about the tissue, until it reaches its final resting position to ablate a tissue mass.

Figure 7:
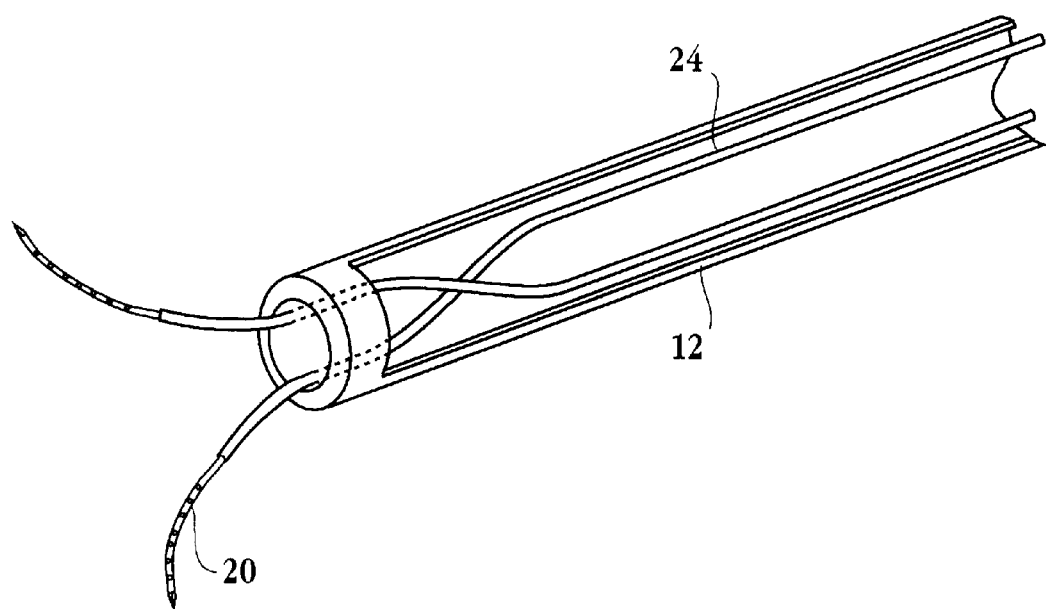
FIG. 7 is a cross-section view of a delivery catheter associated with the invention, with guide tubes positioned at the distal end of the delivery catheter.

Optionally included in the delivery catheter are one or more guide tubes 24, FIG. 7, which serve to direct the expansion of electrodes 20 in the fan pattern as they are advanced out of distal end 16 of the delivery catheter 12. Guide tubes 24 can be made of stainless steel, spring steel and thermal plastics including but not limited to nylon and polyesters, and are of sufficient size and length to accommodate the electrodes to a specific site in the body.

Figure 8:
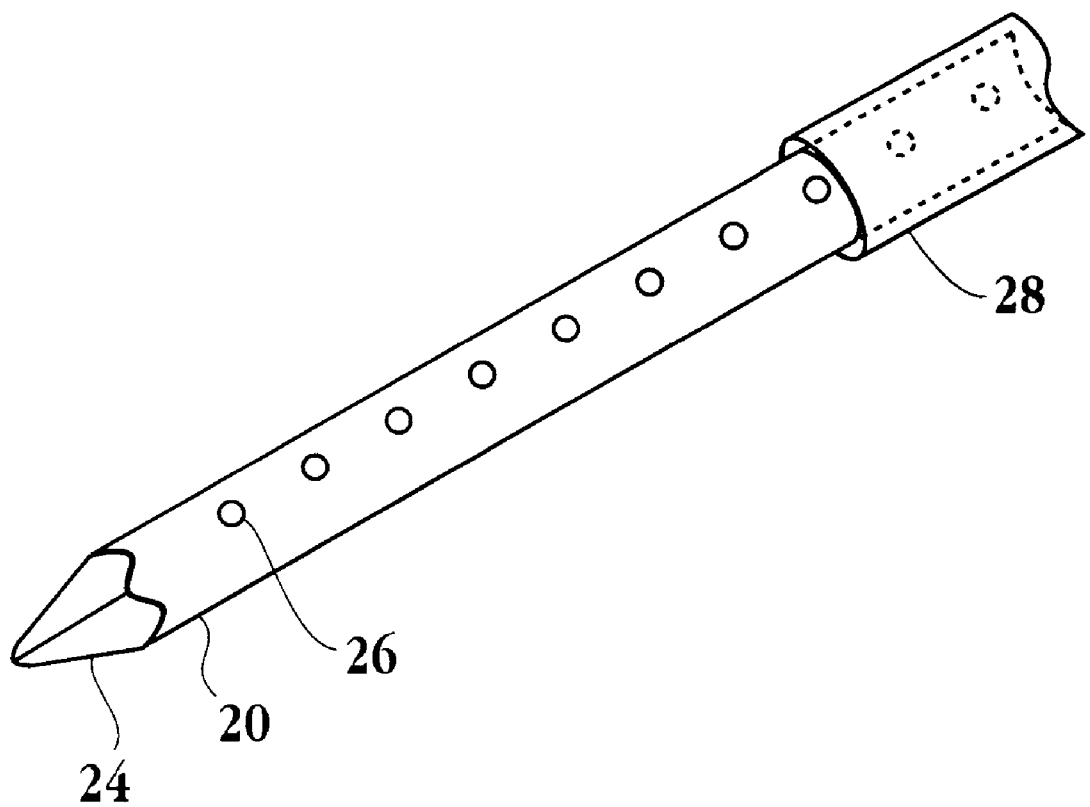
FIG. 8 is a cross-sectional view of an electrode of the invention.

FIG. 8 illustrates one embodiment of electrode 20 with a sharpened distal end 24. By including a tapered, or piercing end 24, the advancement of electrode 20 through tissue is easier. Electrode 20 can be segmented, and include a plurality of fluid distribution ports 26, which can be evenly formed around all or only a portion of electrode 20. Fluid distribution ports 26 are formed in electrode 20 when it is hollow and permit the introduction and flow of a variety of fluidic mediums through electrode 20 to a desired tissue site. Such fluidic mediums include, but are not limited to, electrolytic solutions, pastes or gels, as well as chemotherapeutic agents. Examples of suitable conductive gels are carboxymethyl cellulose gels made from aqueous electrolyte solutions such as physiological saline solutions, and the like.

The size of fluid distribution ports 26 can vary, depending on the size and shape of electrode 20. Also associated with electrode 20 is an adjustable insulator sleeve 28 that is slidable along an exterior surface of electrode 20. Insulator sleeve 28 is advanced and retracted along electrode 20 in order to define the size of a conductive surface of electrode 20. Insulator sleeve 28 is actuated at handle 18 by the physician, and its position along electrode 20 is controlled. When electrode 20 moves out of delivery catheter 12 and into tissue, insulator sleeve 28 can be positioned around electrode 20 as it moves its way through the tissue.

Alternatively, insulator sleeve 28 can be advanced along a desired length of electrode 20 after electrode 20 has been positioned around a targeted mass to be ablated. Insulator sleeve is thus capable of advancing through tissue along with electrode 20, or it can move through tissue without electrode 20 providing the source of movement. Thus, the desired ablation volume is defined by deployed electrodes 20, as well as the positioning of insulator sleeve 28 on each electrode. In this manner, a very precise ablation volume is created. Suitable materials that form insulator sleeve include but are not limited to nylon, polyimides, other thermoplastics, and the like.

Figure 9:
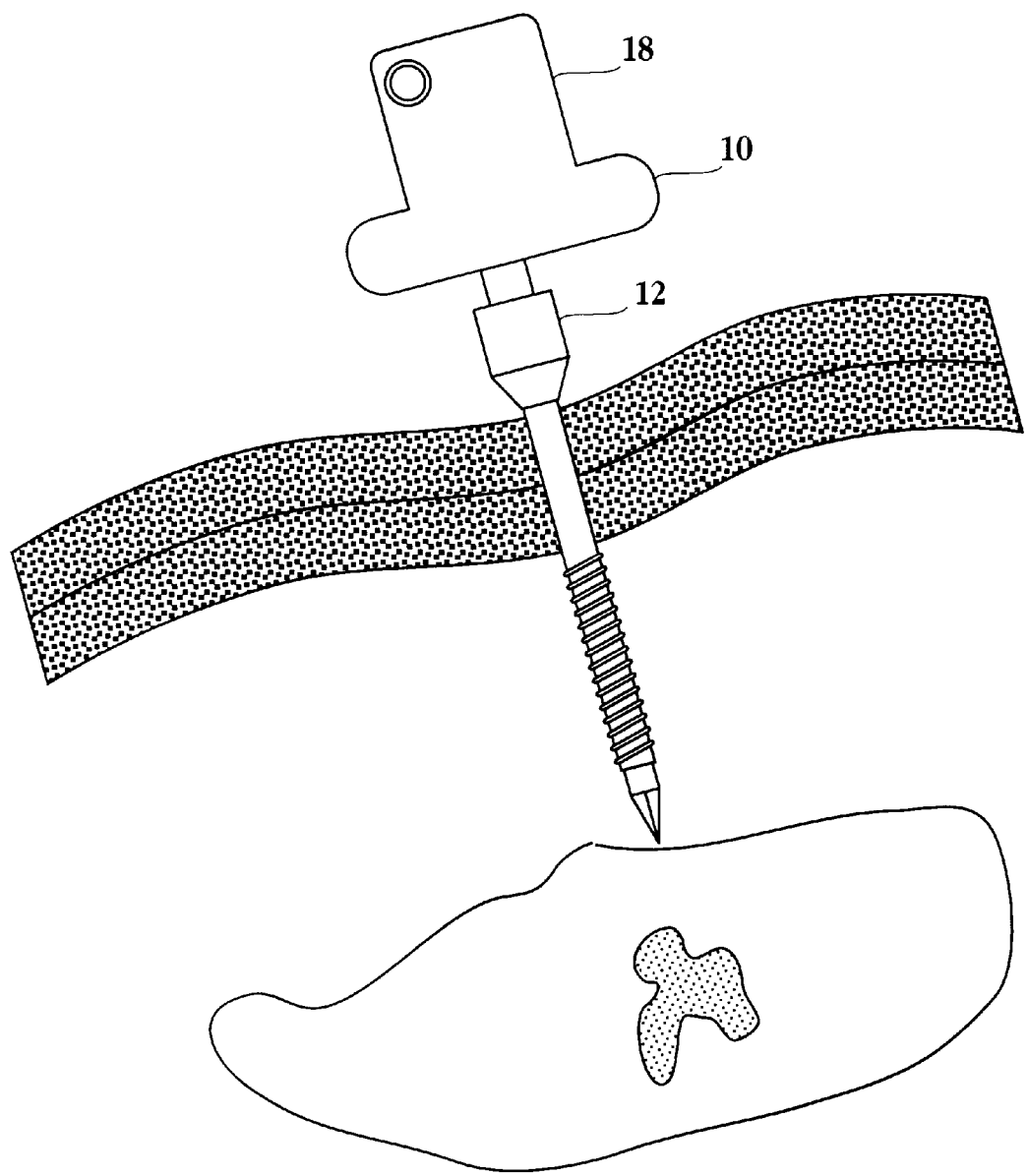
FIG. 9 is a perspective view of the tissue ablation apparatus of the invention shown in FIG. 1, with the delivery catheter being introduced percutaneously through the body and positioned at the exterior, or slightly piercing, a liver with a tumor to be ablated.
Figure 10:
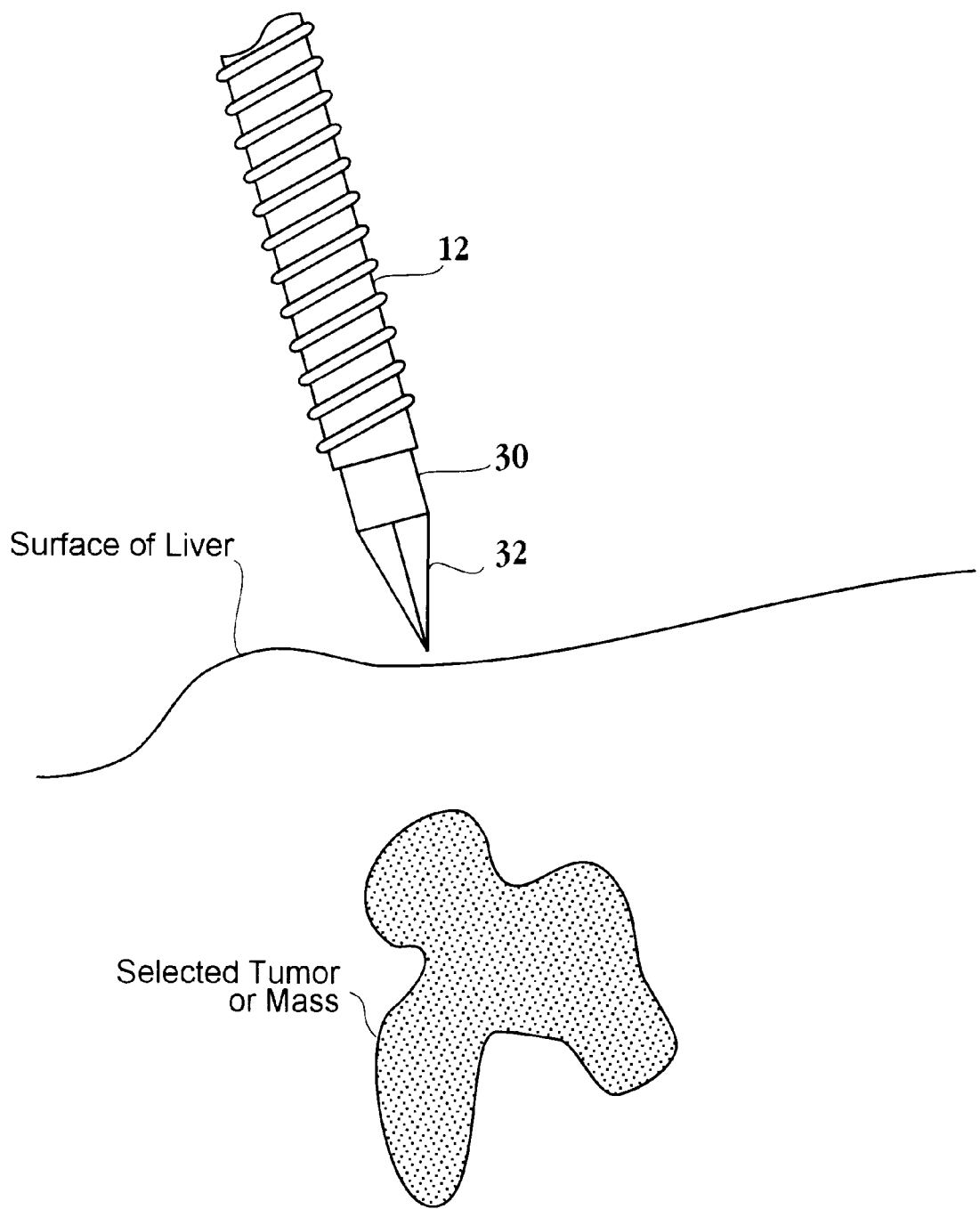
FIG. 10 is a perspective view of the tissue ablation apparatus of the invention with an obturator positioned in the delivery catheter.

FIG. 9 illustrates a percutaneous application of tissue ablation apparatus 10. Tissue ablation apparatus 10 can be used percutaneously to introduce electrodes 20 to the selected tissue mass or tumor. Electrodes 20 can remain in their non-deployed positions while being introduced percutaneously into the body, and delivered to a selected organ which contains the selected mass to be ablated. Delivery catheter 12 is removable from handle 18. When it is removed, electrode deployment device (the plurality of electrodes 20) can be inserted and removed from delivery catheter 12. An obturator 30 is inserted into delivery catheter 12 initially if a percutaneous procedure is to be performed. As shown in FIG. 10, obturator 30 can have a sharpened distal end 32 that pierces tissue and assists the introduction of delivery catheter 12 to a selected tissue site. The selected tissue site can be a body organ with a tumor or other mass, or the actual tumor itself.

Figure 11:
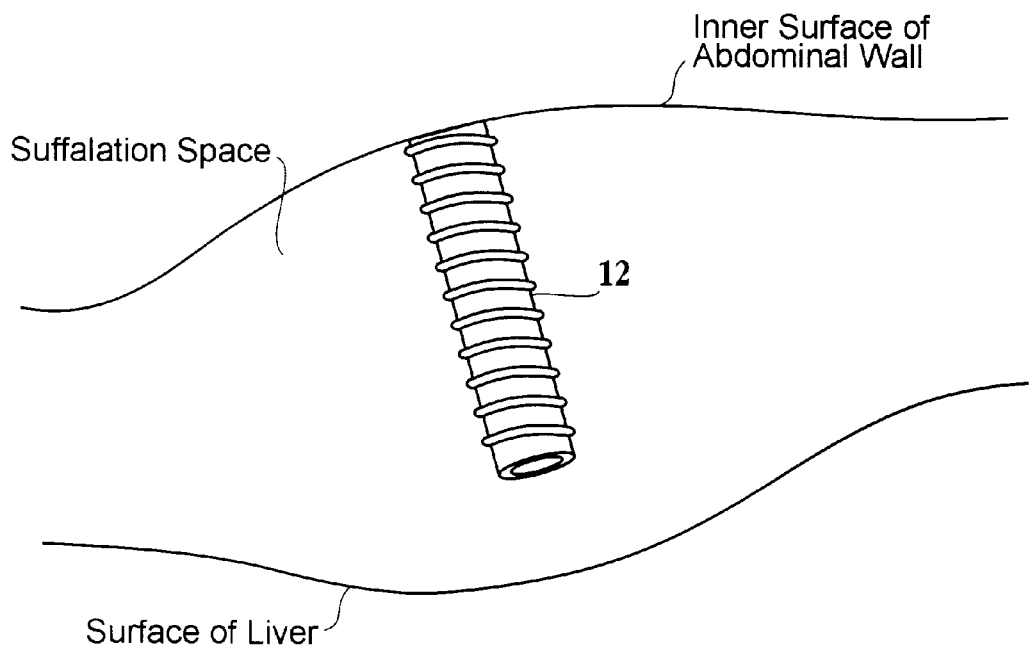
FIG. 11 is a perspective view of the tissue ablation apparatus of the invention shown in FIG. 10, positioned in the body adjacent to the liver, with the obturator removed.
Figure 11:
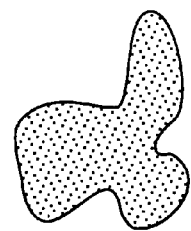
Figure 12:
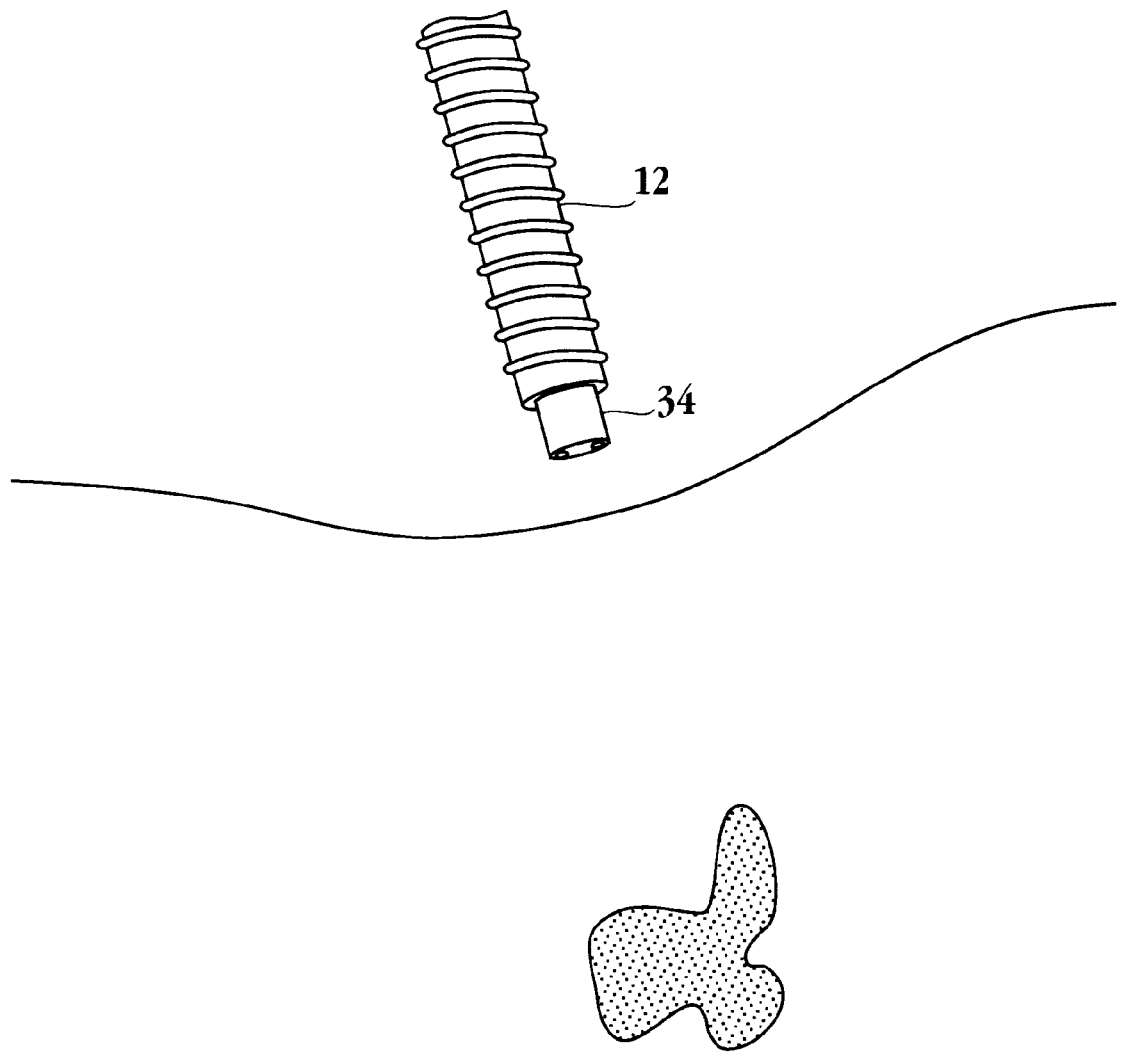
FIG. 12 is a perspective view of the tissue ablation apparatus of the invention shown in FIG. 10, positioned in the body adjacent to the liver, and the electrode deployment apparatus, with an electrode template, is positioned in the delivery catheter in place of the obturator.

Obturator 30 is then removed from delivery catheter 12 (FIG. 11). Electrode deployment device is then inserted into delivery catheter 12, and the catheter is then reattached to handle 18 (FIG. 12). As illustrated in FIG. 12, electrode deployment device can optionally include an electrode template 34 to guide the deployment of electrodes 20 to a surrounding relationship at an exterior of a selected mass in the tissue.

Figure 13:
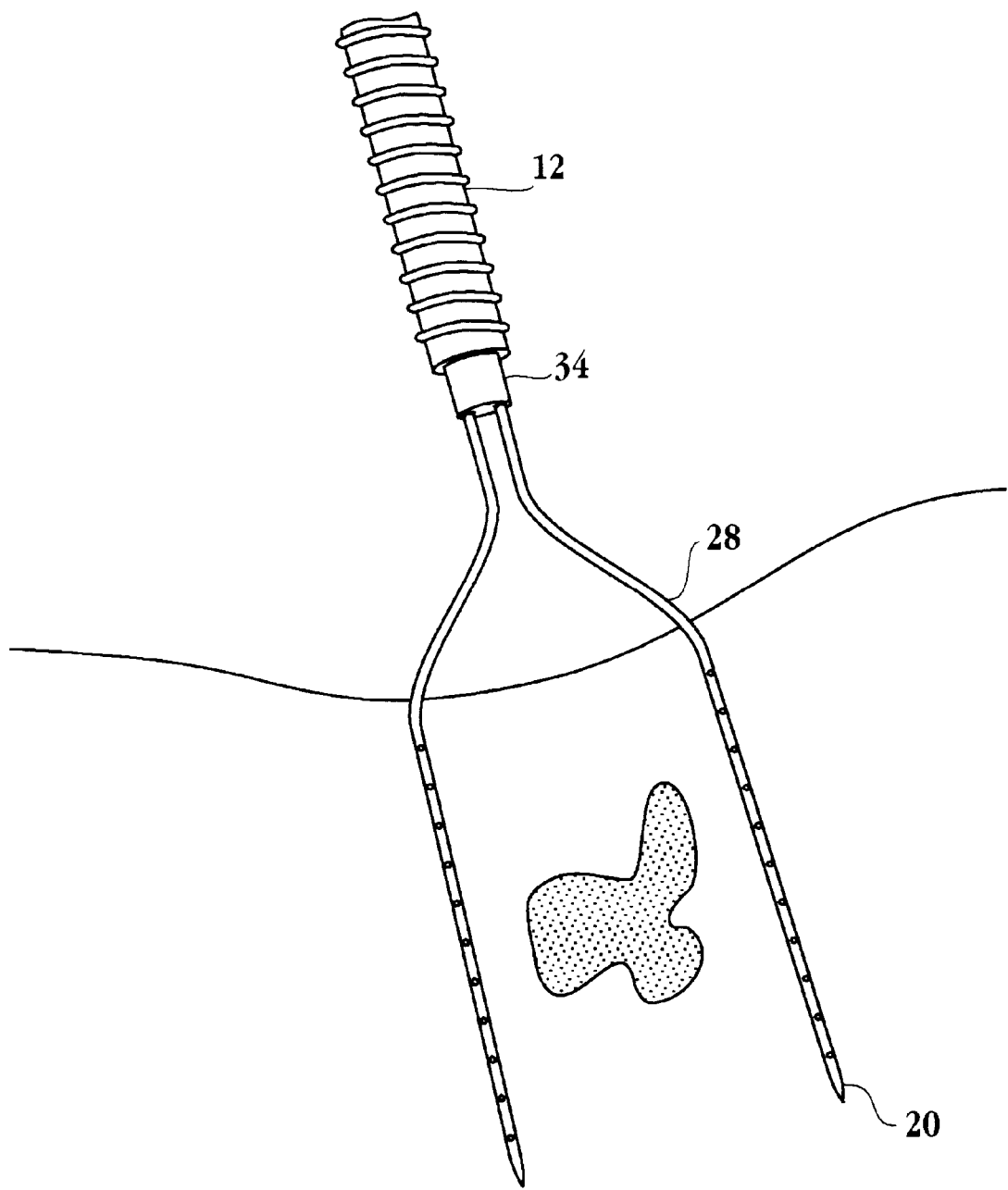
FIG. 13 is a perspective view of the ablation apparatus of the invention, with deployed electrodes surrounding a tumor and defining an ablation volume.

Electrodes 20 are then advanced out of distal end 16 of delivery catheter 12, and become deployed to form a desired ablative volume which surrounds the mass. In FIG. 13, delivery catheter 12 is positioned adjacent to the liver. Electrode deployment device is introduced into delivery catheter 12 with electrode template 34. Electrode deployment device now pierces the liver, and cam 22 advances electrodes 20 out of delivery catheter 12 into deployed positions. Each individual electrode 20 pierces the liver and travels through it until it is positioned in a surrounding relationship to the tumor. The ablative volume is selectable, and determined first by imaging the area to be ablated. The ablative volume is defined by the peripheries of all of the deployed electrodes 20 that surround the exterior of the tumor. Once the volume of ablation is determined, then an electrode set is selected which will become deployed to define the ablation volume. A variety of different factors are important in creating an ablation volume. Primarily, different electrodes 20 will have various degrees of deployment, based on type of electrode material, the level of pre-springing of the electrodes and the geometric configuration of the electrodes in their deployed states. Tissue ablation apparatus 10 permits different electrode 20 sets to be inserted into delivery catheter 12, in order to define a variety of ablation volumes.

Figure 14:
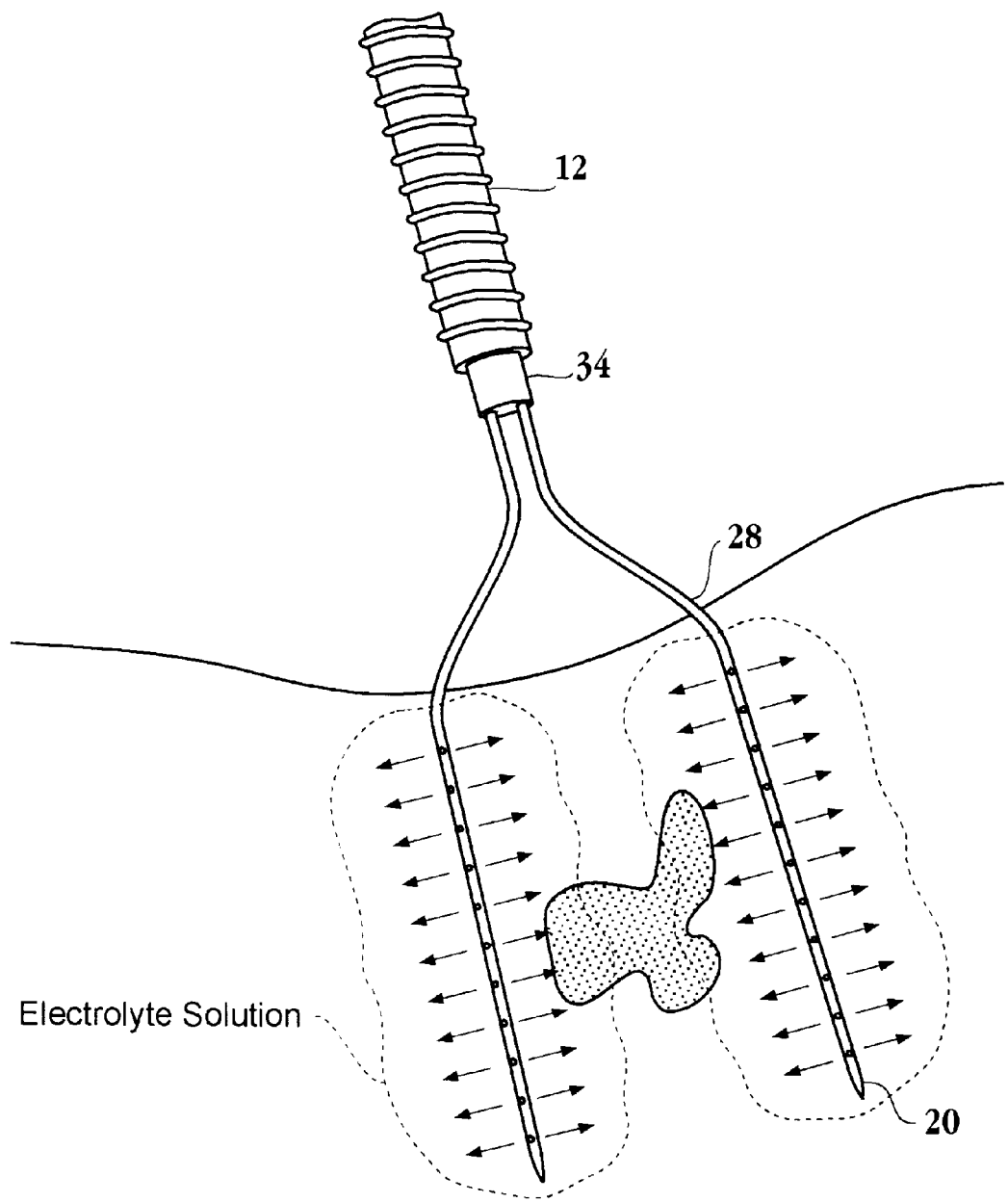
FIG. 14 is a perspective view of the tissue ablation apparatus of the invention shown in FIG. 10, positioned in the body adjacent to the liver, with deployed electrodes surrounding a tumor and infusing a solution to the tumor site during a pre-ablation procedure.
Figure 15:
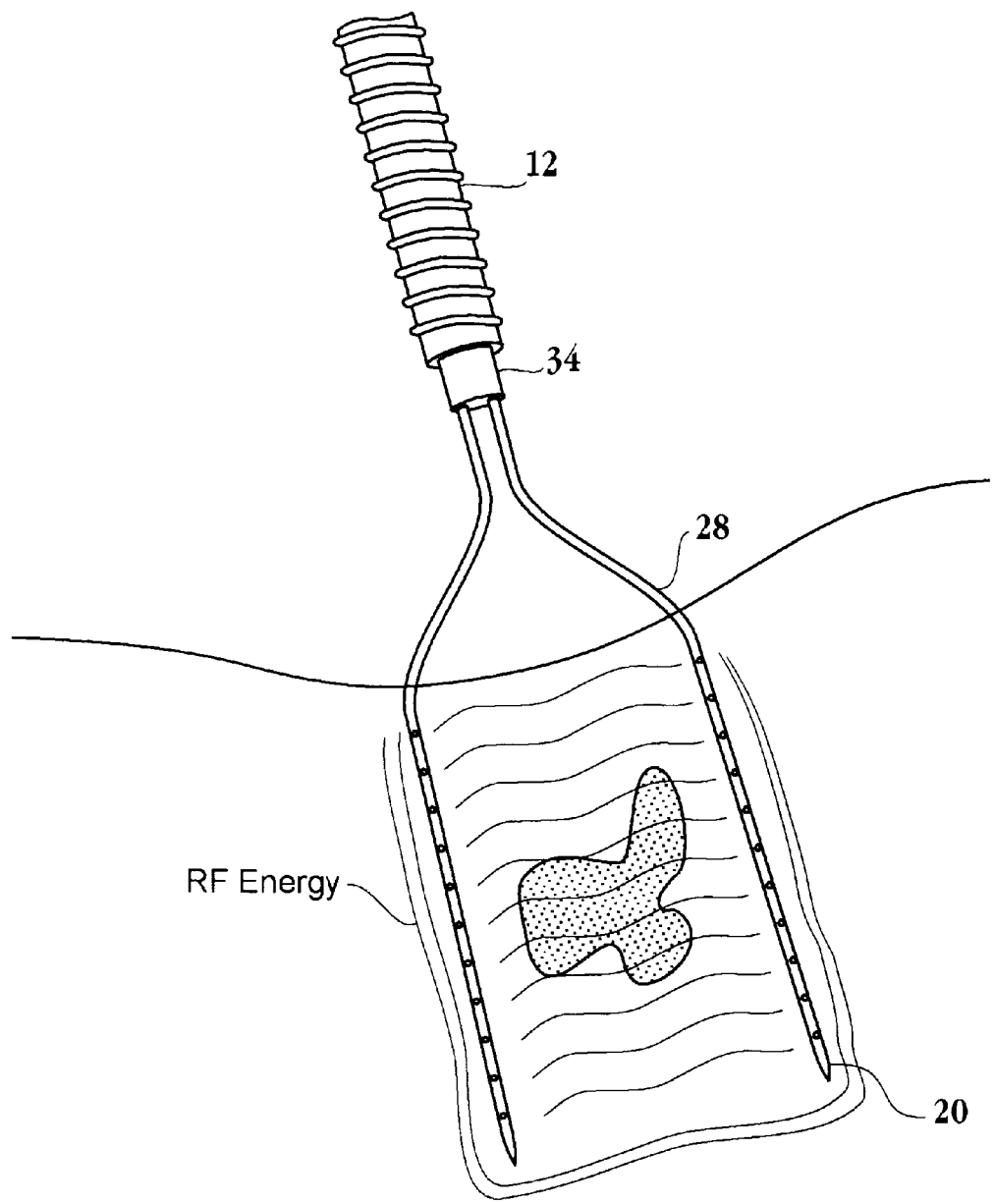
FIG. 15 is a perspective view of the tissue ablation apparatus of the invention shown in FIG. 10, illustrating application of RF energy to the tumor.
Figure 16:
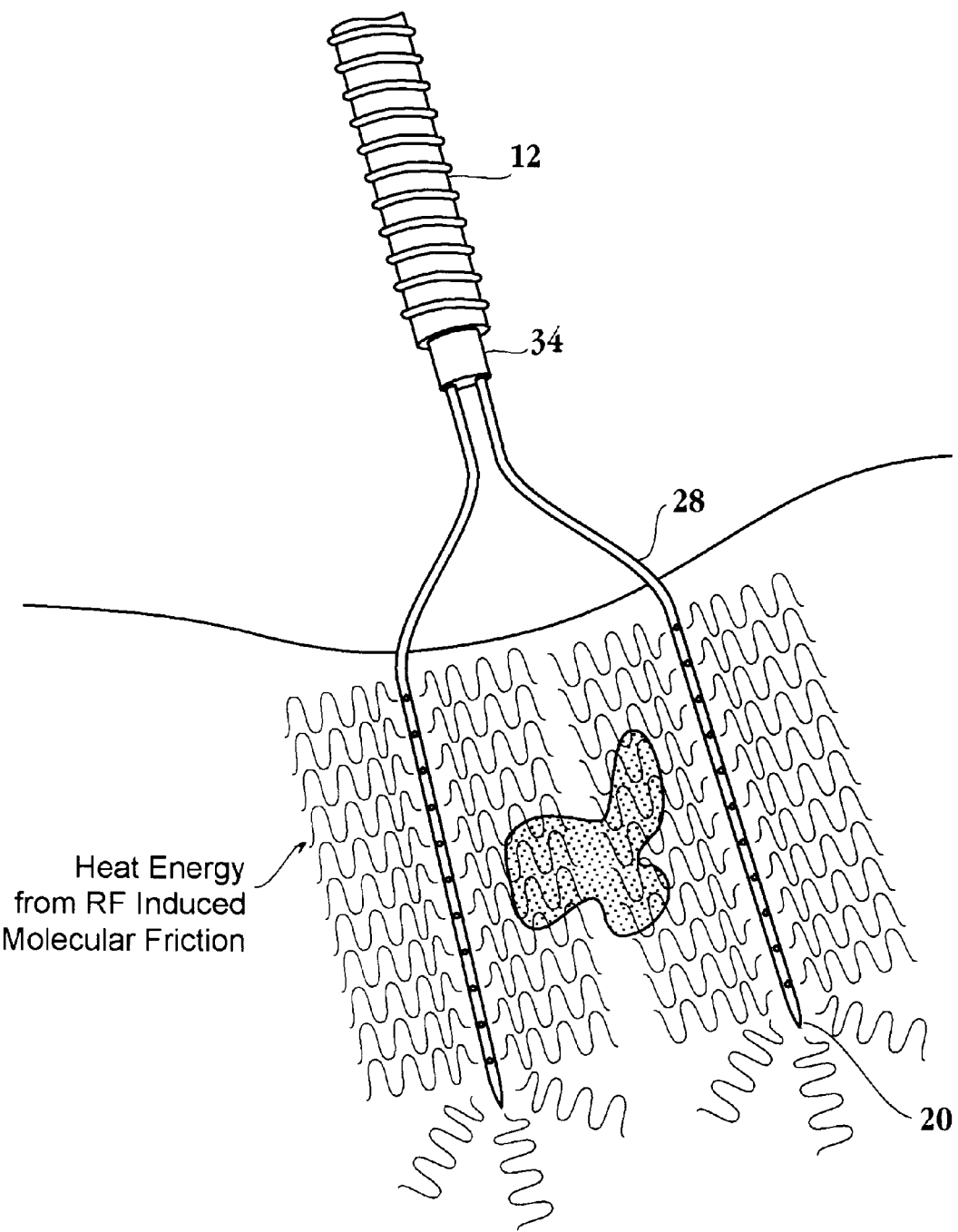
FIG. 16 is a perspective view of the tissue ablation apparatus of the invention, illustrating the electro-desiccation of the tumor.

Prior to ablation of the tumor, a pre-ablation step can be performed. A variety of different solutions, including electrolytic solutions such as saline, can be introduced to the tumor site, as shown in FIG. 14. FIG. 15 illustrates the application of RF energy to the tumor. Electrode insulator 28 is positioned on portions of electrodes 20 where there will be no ablation. This further defines the ablation volume. The actual electro-desiccation of the tumor, or other targeted masses or tissues, is shown in FIG. 16. Again, deployed electrodes 20, with their electrode insulators 28 positioned along sections of the electrodes, define the ablation volume, and the resulting amount of mass that is desiccated.

Figure 17:
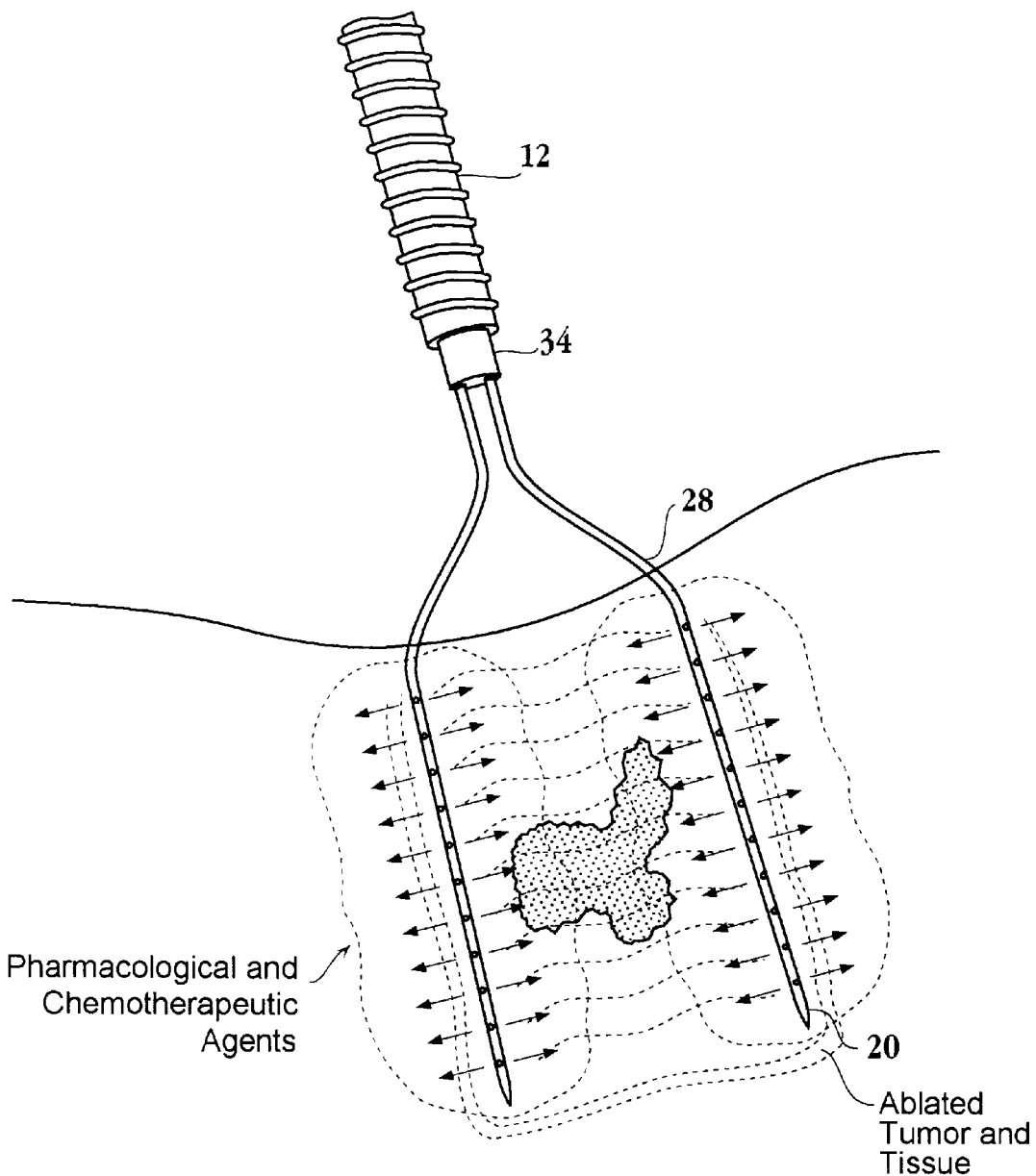
FIG. 17 is a perspective view of the tissue ablation apparatus of the invention, illustrating the instillation of solutions to the tumor site during a post-ablation procedure.
Figure 18:
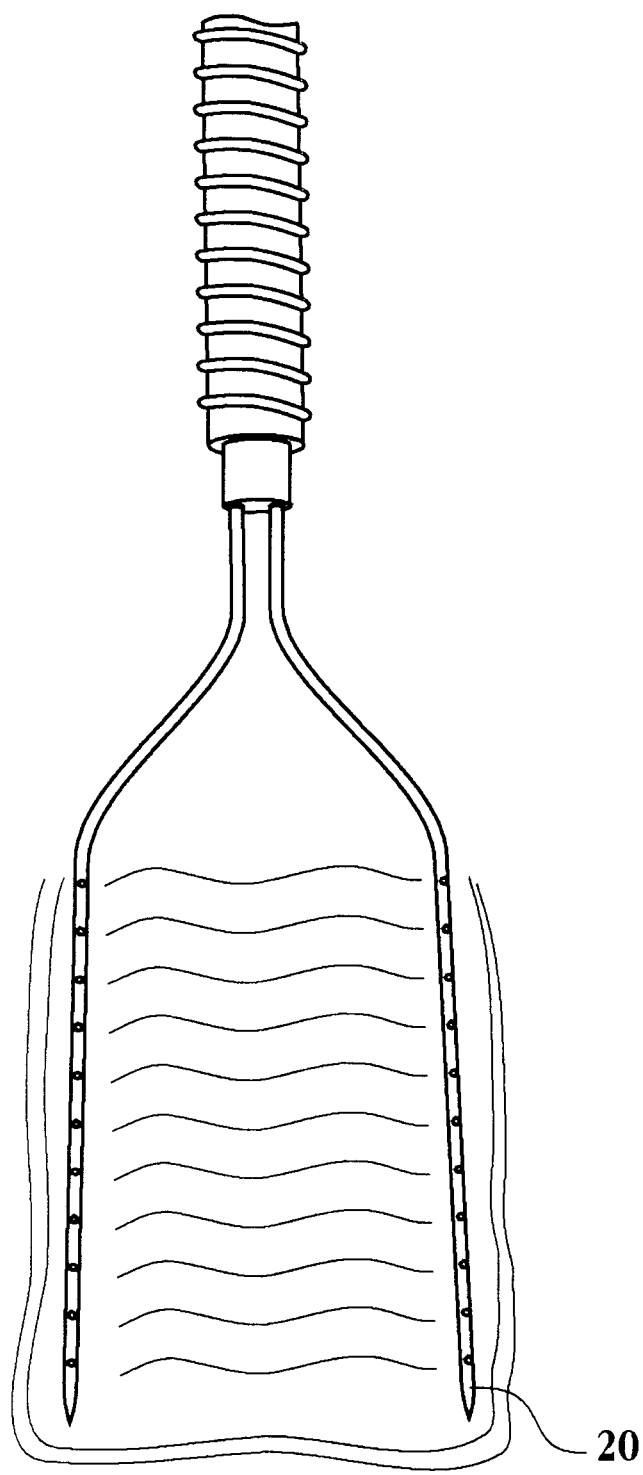
FIG. 18 illustrates bipolar ablation between electrodes of the invention.

Optionally following desiccation, electrodes 20 can introduce a variety of solutions in a post-ablation process. This step is illustrated in FIG. 17. Suitable solutions include but are not limited to chemotherapeutic agents.

Figure 19:
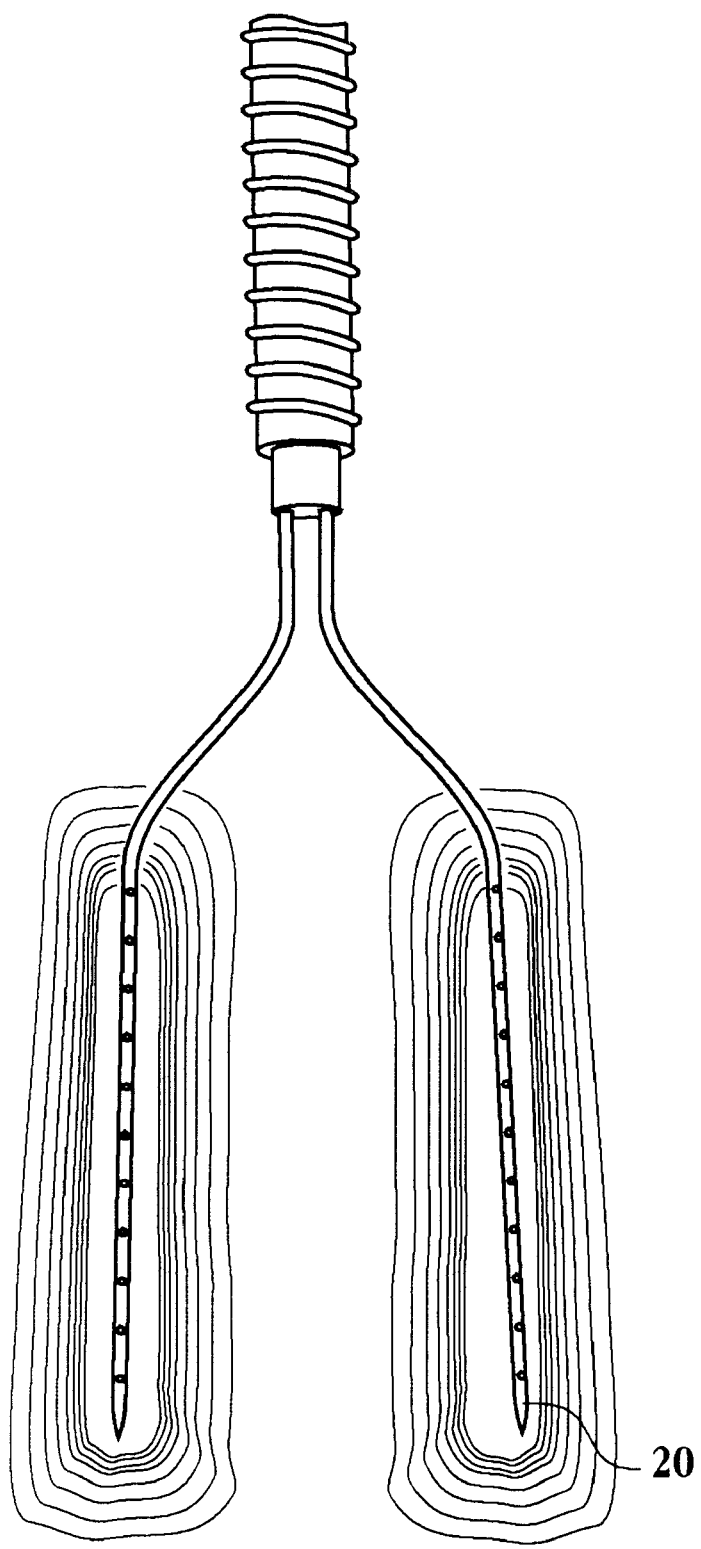
FIG. 19 illustrates monopolar ablation between electrodes of the invention.

FIG. 8 illustrates tissue ablation apparatus 10 operated in a bipolar mode. Its monopolar operation is shown in FIG. 19. Each of the plurality of electrodes 20 can play different roles in the ablation process. There can be polarity shifting between the different electrodes.

Figure 20:
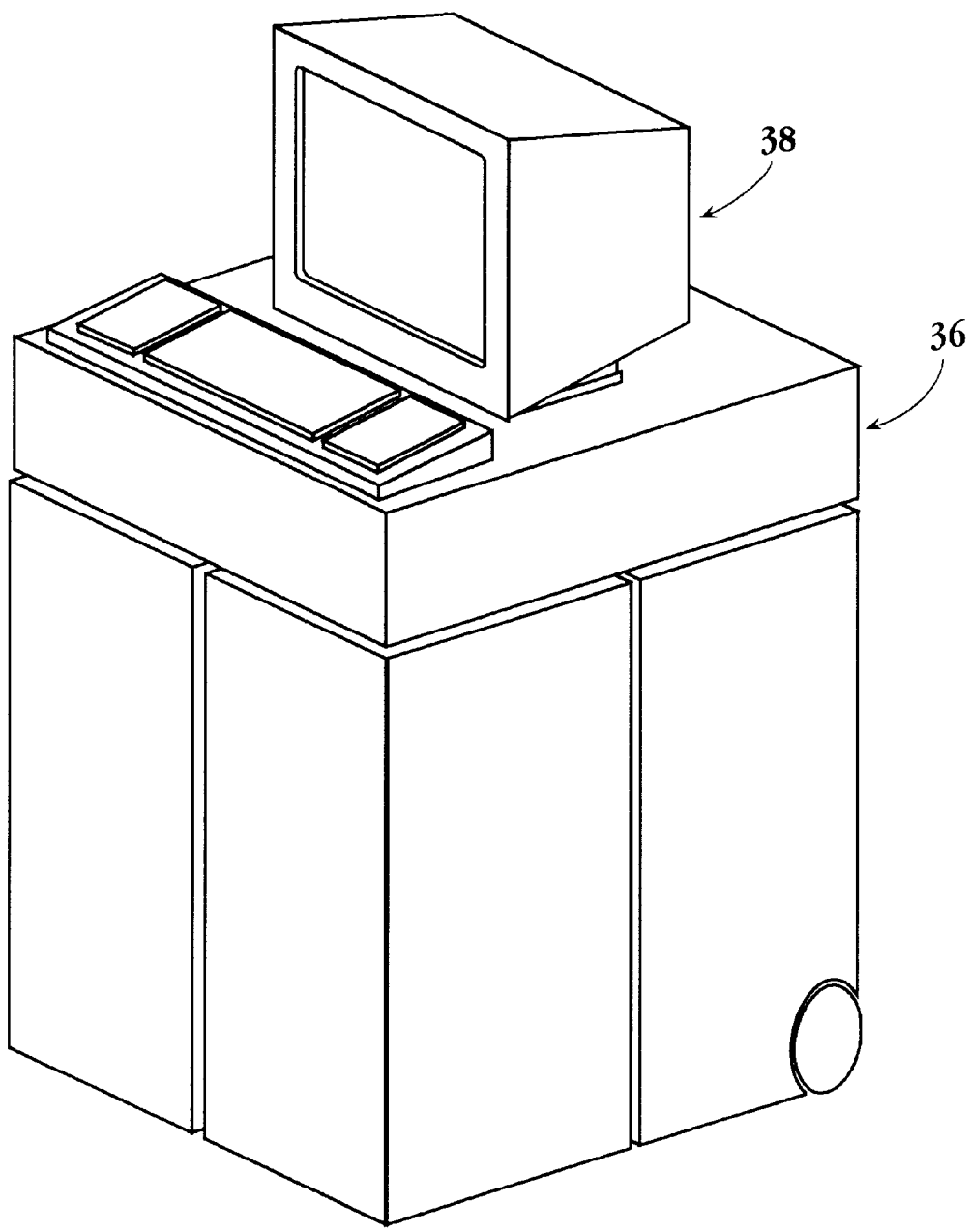
FIG. 20 is a perspective view of an ablation system of the invention, including RF and ultrasound modules, and a monitor.

A tissue ablation system 36, which can be modular, is shown in FIG. 20 and can include a display 38. Tissue ablation system 36 can also include an RF energy source, microwave source, ultrasound source, visualization devices such as cameras and VCR's, electrolytic and chemotherapeutic solution sources, and a controller which can be used to monitor temperature or impedance. One of the deployed electrodes 20 can be a microwave antenna coupled to a microwave source. This electrode can initially be coupled to RF power source 42 and is then switched to the microwave source.

Figure 21:
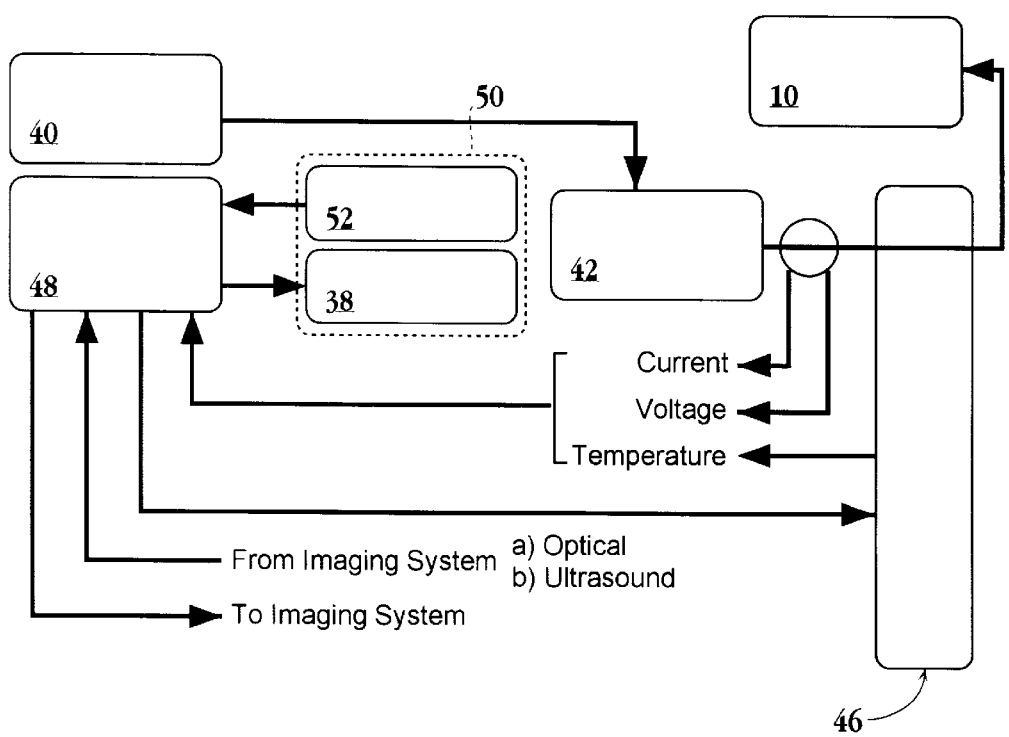
FIG. 21 is a block diagram of the ablation system of the invention.

Referring now to FIG. 21, a power supply 40 delivers energy into RF power generator (source) 42 and then to electrodes 20 of tissue ablation apparatus 10. A multiplexer 46 measures current, voltage and temperature (at numerous temperature sensors which can be positioned on electrodes 20). Multiplexer 46 is driven by a controller 48, which can be a digital or analog controller, or a computer with software. When controller 48 is a computer, it can include a CPU coupled through a system bus. This system can include a keyboard, disk drive, or other non-volatile memory systems, a display, and other peripherals, as known in the art. Also coupled to the bus are a program memory and a data memory.

An operator interface 50 includes operator controls 52 and display 38. Controller 48 is coupled to imaging systems, including ultrasound transducers, temperature sensors, and viewing optics and optical fibers, if included.

Current and voltage are used to calculate impedance. Diagnostics are done through ultrasound, CT scanning, or other methods known in the art. Imaging can be performed before, during and after treatment.

Temperature sensors measure voltage and current that is delivered. The output of these sensors is used by controller 48 to control the delivery of RF power. Controller 48 can also control temperature and power. The amount of RF energy delivered controls the amount of power. A profile of power delivered can be incorporated in controller 38, as well as a pre-set amount of energy to be delivered can also be profiled.

Feedback can be the measurement of impedance or temperature, and occurs either at controller 48 or at electromagnetic energy source 42, e.g., RF or microwave, if it incorporates a controller. For impedance measurement, this can be achieved by supplying a small amount of non-ablation RF energy. Voltage and current are then measured.

Circuitry, software and feedback to controller 48 result in process control and are used to change, (i) power, including RF, ultrasound, and the like, (ii) the duty cycle (on-off and wattage), (iii) monopolar or bipolar energy delivery, (iv) and electrolytic solution delivery, flow rate and pressure and (v) determine when ablation is completed through time, temperature and/or impedance. These process variables can be controlled and varied based on temperature monitored at multiple sites, and impedance to current flow that is monitored, indicating changes in current carrying capability of the tissue during the ablative process.

Referring now to FIGS. 22(*a*). 22(*b*), 22(*c*), 22 and 24 an RF treatment apparatus 110 is illustrated which can be used to ablate a selected tissue mass, including but not limited to a tumor, or treat the mass by hyperthermia. Treatment apparatus 110 includes a catheter 112 with a catheter lumen in which different devices are introduced and removed. An insert 114 is removably positioned in the catheter lumen. Insert 114 can be an introducer, a needle electrode, and the like.

When insert 114 is an introducer, including but not limited to a guiding or delivery catheter, it is used as a means for puncturing the skin of the body, and advancing catheter 112 to a desired site. Alternatively, insert 114 can be both an introducer and an electrode adapted to receive RF current for tissue ablation and hyperthermia.

If insert 114 is not an electrode, then a removable electrode 116 is positioned in insert 114 either during or after treatment apparatus 110 has been introduced percutaneously to the desired tissue site. Electrode 116 has an electrode distal end that advances out of an insert distal end. In this deployed position, RF energy is introduced to the tissue site along a conductive surface of electrode 116.

Electrode 116 can be included in treatment apparatus 110, and positioned within insert 114, while treatment apparatus 110 is being introduced to the desired tissue site. The distal end of electrode 116 can have substantially the same geometry as the distal end of insert 114 so that the two ends are essentially flush. Distal end of electrode 116, when positioned in insert 114 as it is introduced through the body, serves to block material from entering the lumen of insert 114. The distal end of electrode 116 essentially can provide a plug type of function.

Electrode 116 is then advanced out of a distal end of insert 114, and the length of an electrode conductive surface is defined, as explained further in this specification. Electrode 116 can advance out straight, laterally or in a curved manner out of distal end of insert 114. Ablative or hyperthermia treatment begins when two electrodes 116 are positioned closely enough to effect bipolar treatment of the desired tissue site or tumor. A return electrode attaches to the patients skin. Operating in a bipolar mode, selective ablation of the tumor is achieved. However, it will be appreciated that the present invention is suitable for treating, through hyperthermia or ablation, different sizes of tumors or masses. The delivery of RF energy is controlled and the power at each electrode is maintained, independent of changes in voltage or current. Energy is delivered slowly at low power. This minimizes desiccation of the tissue adjacent to the electrodes 116, permitting a wider area of even ablation. In one embodiment, 8 to 14 W of RF energy is applied in a bipolar mode for 10 to 25 minutes. An ablation area between electrodes 116 of about 2 to 6 cm is achieved.

Treatment apparatus 110 can also include a removable introducer 118 which is positioned in the insert lumen instead of electrode 116. Introducer 118 has an introducer distal end that also serves as a plug, to minimize the entrance of material into the insert distal end as it advances through a body structure. Introducer 118 is initially included in treatment apparatus, and is housed in the lumen of insert 114, to assist the introduction of treatment apparatus 110 to the desired tissue site. Once treatment apparatus 110 is at the desired tissue site, then introducer 118 is removed from the insert lumen, and electrode 116 is substituted in its place. In this regard, introducer 118 and electrode 116 are removable to and from insert 114.

Also included is an insulator sleeve 120 coupled to an insulator slide 122. Insulator sleeve 120 is positioned in a surrounding relationship to electrode 116. Insulator slide 122 imparts a slidable movement of the insulator sleeve along a longitudinal axis of electrode 116 in order to define an electrode conductive surface what begins at an insulator sleeve distal end.

A thermal sensor 124 can be positioned in or on electrode 116 or introducer 118. A thermal sensor 126 is positioned on insulator sleeve 120. In one embodiment, thermal sensor 124 is located at the distal end of introducer 118, and thermal sensor 126 is located at the distal end of insulator sleeve 120, at an interior wall which defines a lumen of insulator sleeve 120. Suitable thermal sensors include a T type thermocouple with copper constantene, J type, E type, K type, thermistors, fiber optics, resistive wires, thermocouples IR detectors, and the like. It will be appreciated that sensors 124 and 126 need not be thermal sensors.

Catheter 112, insert 114, electrode 116 and introducer 118 can be made of a variety of materials. In one embodiment, catheter 112 is black anodizid aluminum, 0.5 inch, electrode 116 is made of stainless steel, 18 gauge, introducer 118 is made of stainless steel, 21 gauge, and insulator sleeve 120 is made of polyimide.

By monitoring temperature, RF power delivery can be accelerated to a predetermined or desired level. Impedance is used to monitor voltage and current. The readings of thermal sensors 124 and 126 are used to regulate voltage and current that is delivered to the tissue site. The output for these sensors is used by a controller, described further in this specification, to control the delivery of RF energy to the tissue site. Resources, which can be hardware and/or software, are associated with an RF power source, coupled to electrode 116 and the return electrode. The resources are associated with thermal sensors 124 and 125, the return electrode as well as the RF power source for maintaining a selected power at electrode 116 independent of changes in voltage or current. Thermal sensors 124 and 126 are of conventional design, including but not limited to thermistors, thermocouples, resistive wires, and the like.

Electrode 116 is preferably hollow and includes a plurality of fluid distribution ports 128 from which a variety of fluids can be introduced, including electrolytic solutions, chemotherapeutic agents, and infusion media.

Figure 23:
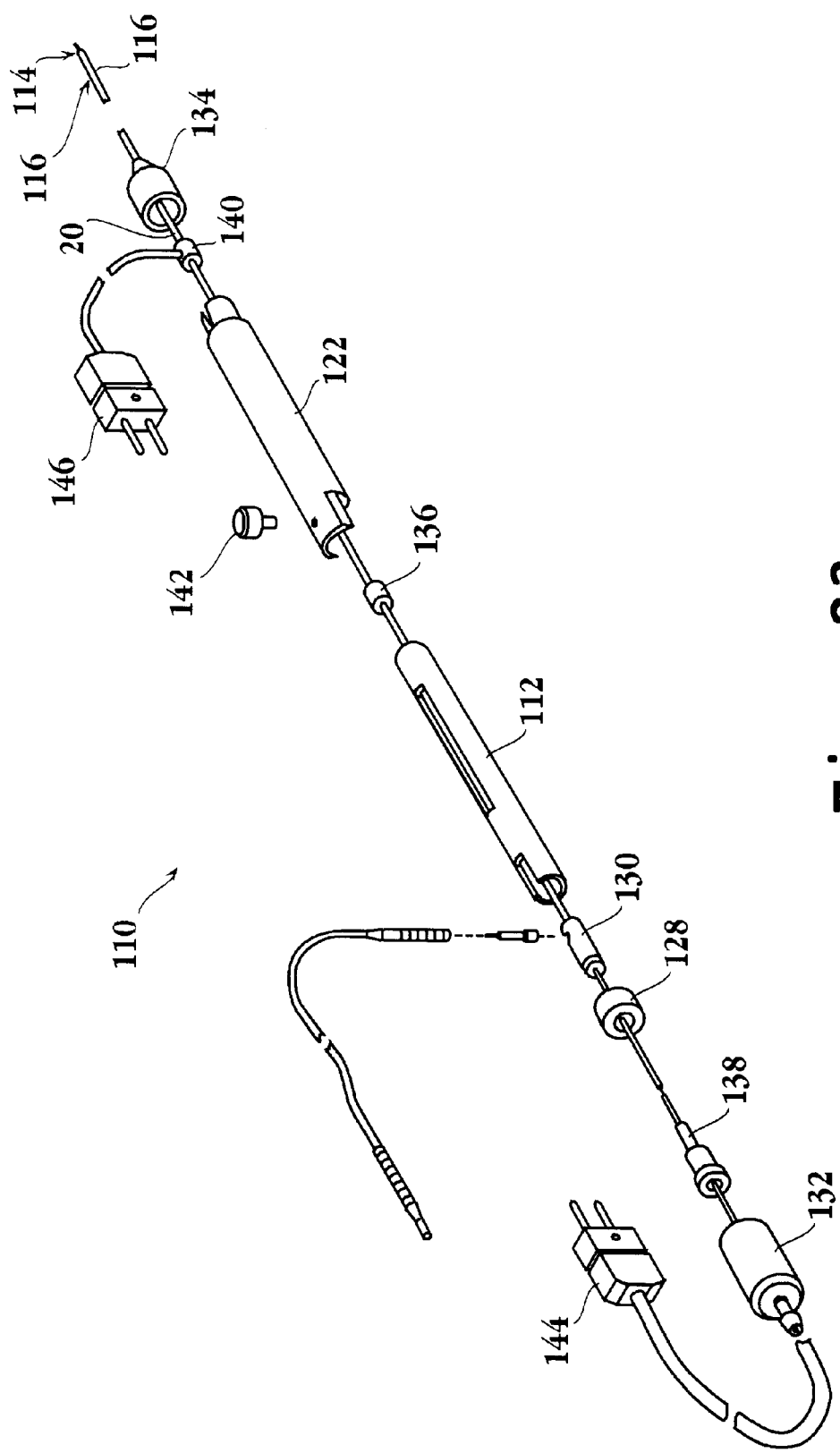
FIG. 23 is an exploded view of an RF treatment apparatus of the invention.
Figure 24:
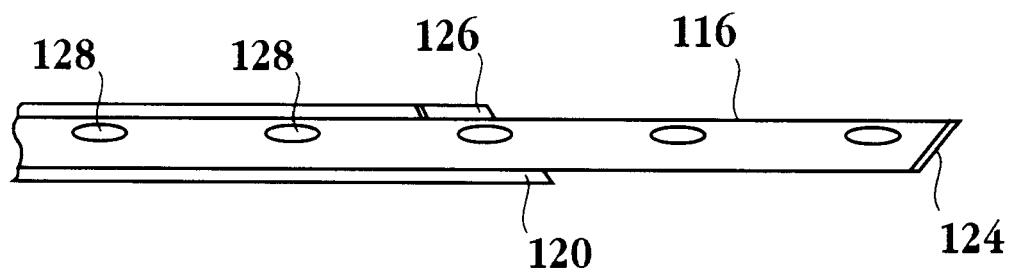
FIG. 24 is a cross-sectional view of the RF treatment apparatus of the invention illustrating the electrode, insulation sleeve and the associated thermal sensors.

A specific embodiment of the RF treatment device 110 is illustrated in FIG. 23. Included is an electrode locking cap 128, an RF coupler 310, an introducer locking cap 312, insulator slide 122, catheter body 112, insulator retainer cap 134, insulator locking sleeve 136, a luer connector 138, an insulator elbow connector 140, an insulator adjustment screw 142, a thermocouple cable 144 for thermal sensor 126, a thermocouple cable 146 for thermal sensor 124 and a luer retainer 148 for an infusion device 150.

In another embodiment of RF treatment apparatus 110, electrode 116 is directly attached to catheter 112 without insert 114. Introducer 118 is slidably positioned in the lumen of electrode 116. Insulator sleeve 120 is again positioned in a surrounding relationship to electrode 116 and is slidably moveable along its surface in order to define the conductive surface. Thermal sensors 124 and 126 are positioned at the distal ends of introducer 118 and insulator sleeve 120. Alternatively, thermal sensor 124 can be positioned on electrode 116, such as at its distal end. The distal ends of electrode 116 and introducer 118 can be sharpened and tapered. This assists in the introduction of RF treatment apparatus to the desired tissue site. Each of the two distal ends can have geometries that essentially match. Additionally, distal end of introducer 118 can an essentially solid end in order to prevent the introduction of material into the lumen of catheter 116.

In yet another embodiment of RF treatment apparatus 110, infusion device 150 remains implanted in the body after catheter 112, electrode 116 and introducer 118 are all removed. This permits a chemotherapeutic agent, or other infusion medium, to be easily introduced to the tissue site over an extended period of time without the other devices of RF treatment apparatus 110 present. These other devices, such as electrode 116, can be inserted through infusion device 150 to the tissue site at a later time for hyperthermia or ablation purposes. Infusion device 150 has an infusion device lumen and catheter 112 is at least partially positioned in the infusion device lumen. Electrode 116 is positioned in the catheter lumen, in a fixed relationship to catheter 112, but is removable from the lumen. Insulator sleeve 120 is slidably positioned along a longitudinal axis of electrode 116. Introducer 118 is positioned in a lumen of electrode 116 and is removable therefrom. A power source is coupled to electrode 116. Resources are associated with thermal sensors 124 and 126, voltage and current sensors that are coupled to the RF power source for maintaining a selected power at electrode 116.

Figure 22A:
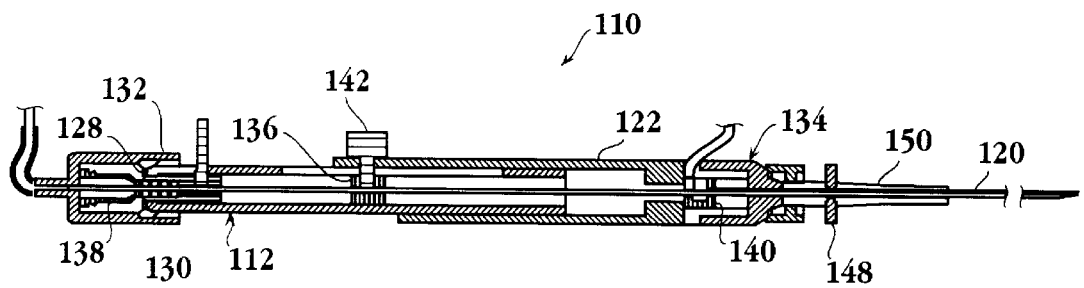
FIG. 22(a) is a cross-sectional view of an RF treatment apparatus of the invention.
Figure 22B:
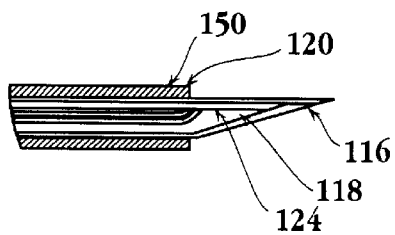
FIG. 22(b) is a close up cross-sectional view of the distal end of the RF treatment apparatus of FIG. 22(a).

The distal end of RF treatment apparatus 110 is shown in FIG. 22(b). Introducer 118 is positioned in the lumen of electrode 116, which can be surrounded by insulator sleeve 120, all of which are essentially placed in the lumen of infusion device 150. It will be appreciated, however, that in FIG. 22(b) insert 114 can take the place of electrode 116, and electrode 116 can be substituted for introducer 118.

Figure 22C:
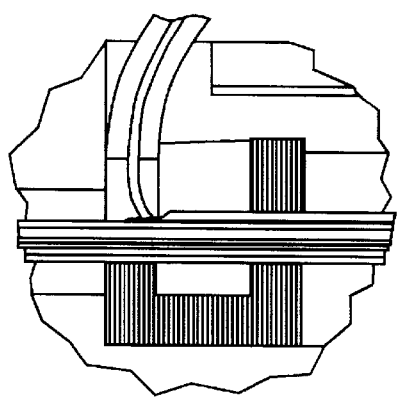
FIG. 22(c) is a close up cross-sectional view of the RF treatment apparatus of FIG. 22(a), illustrating the proximal end of the insulation sleeve and a thermocouple associated with the insulation sleeve.
Figure 22D:
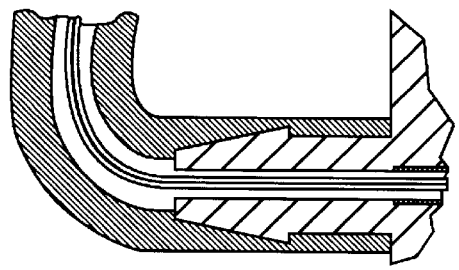
FIG. 22(d) is a close up cross-sectional view of the RF treatment apparatus of FIG. 22(a), illustrating the proximal end of the RF treatment apparatus of FIG. 22(a).

The distal end of insulator sleeve 120 is illustrated in FIG. 22(c). Thermal sensor 126 is shown as being in the form of a thermocouple. In FIG. 22(d), thermal sensor 124 is also illustrated as a thermocouple that extends beyond a distal end of introducer 118, or alternative a distal end of electrode 116.

Figure 25A:
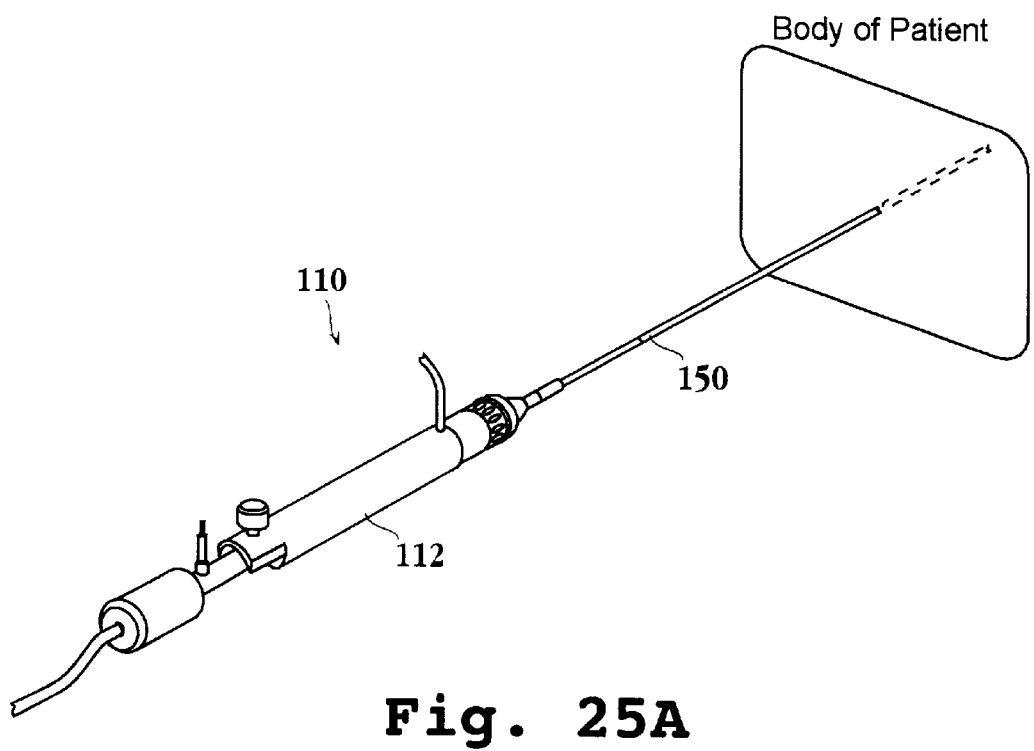
FIG. 25(a) is a perspective view of the RF treatment apparatus of the invention with the infusion device mounted at the distal end of the catheter.
Figure 25B:
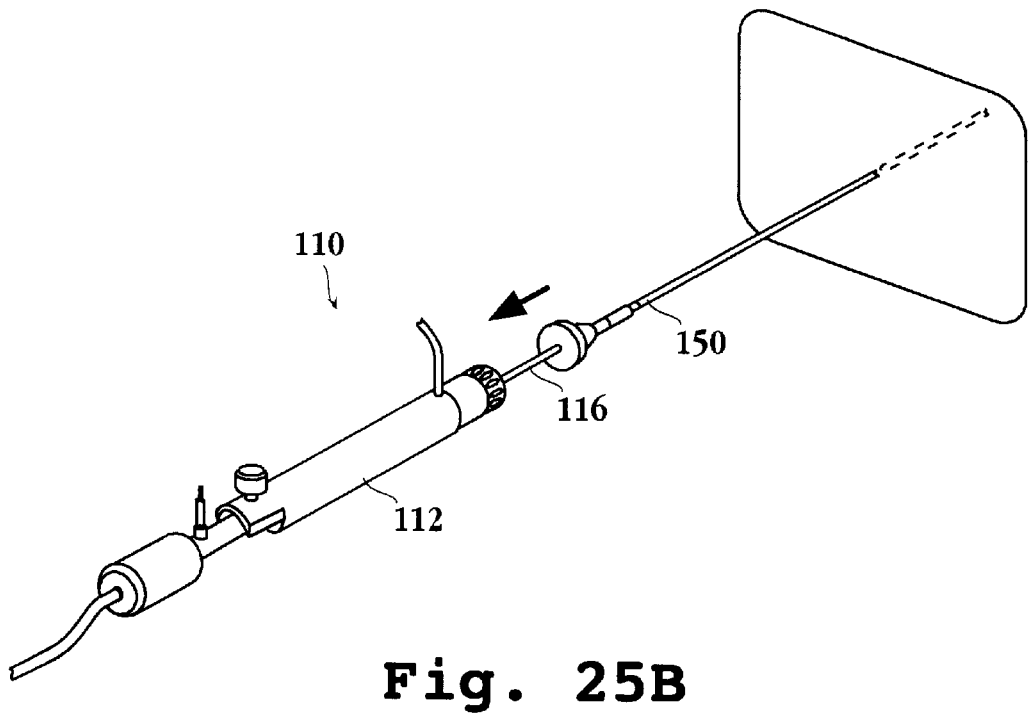
FIG. 25b is a perspective view of the RF treatment apparatus of FIG. 25(a) illustrating the removal of the catheter, and electrode attached to the distal end of the electrode, from the infusion device which is left remaining in the body.

Referring now to FIGS. 25(a) and 25(b), infusion device 150 is attached to the distal end of catheter 112 and retained by a collar. The collar is rotated, causing catheter 112 to become disengaged from infusion device 150. Electrode 116 is attached to the distal end of catheter 112. Catheter 112 is pulled away from infusion device 150, which also removes electrode 116 from infusion device 150. Thereafter, only infusion device 150 is retained in the body. While it remains placed, chemotherapeutic agents can be introduced through infusion device 150 to treat the tumor site. Additionally, by leaving infusion device 150 in place, catheter 112 with electrode 116 can be reintroduced back into the lumen of infusion device 150 at a later time for additional RF treatment in the form of ablation or hyperthermia.

Figure 26A:
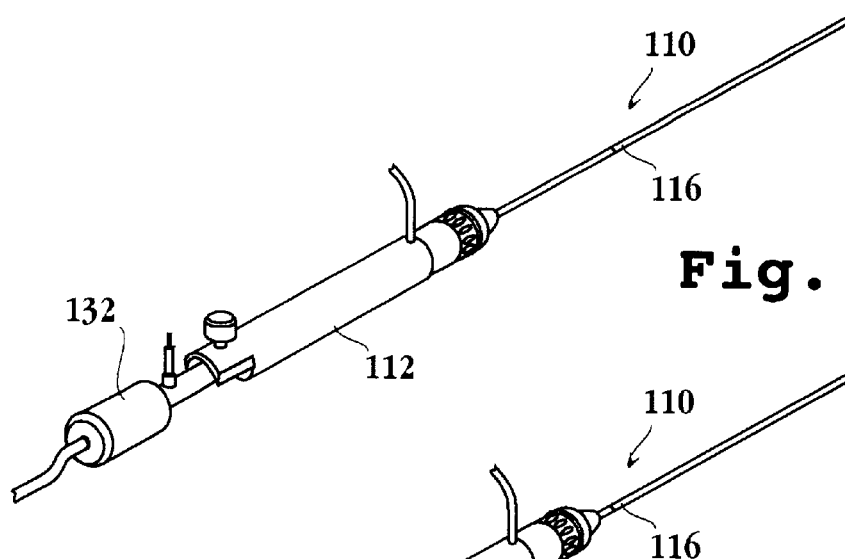
FIG. 26(a) is a perspective view of the RF treatment apparatus of the invention with the electrode mounted at the distal end of the catheter.
Figure 26B:
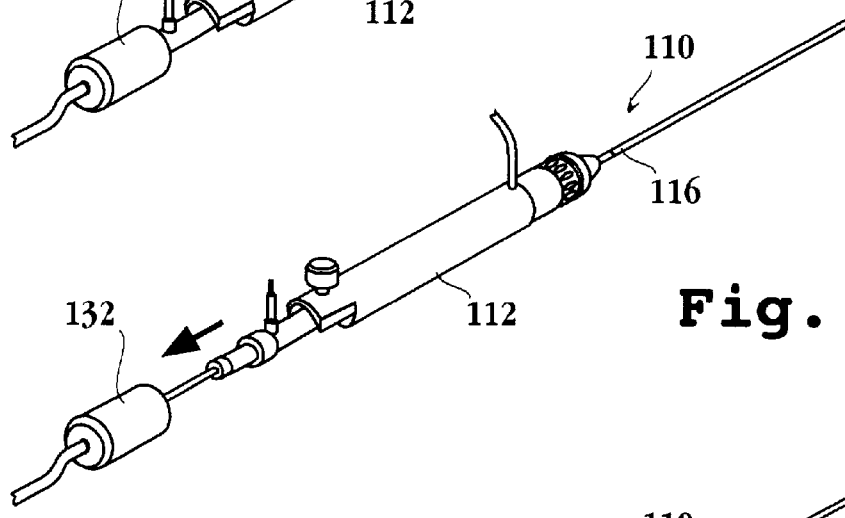
FIG. 26(b) is a perspective view of the RF treatment apparatus of FIG. 26(a) illustrating the removal of the introducer from the lumen of the electrode.

In FIG. 26(a), electrode 116 is shown as attached to the distal end of catheter 112. Introducer 118 is attached to introducer locking cap 132 which is rotated and pulled away from catheter 112. As shown in FIG. 26(b) this removes introducer 118 from the lumen of electrode 116.

Figure 27A:
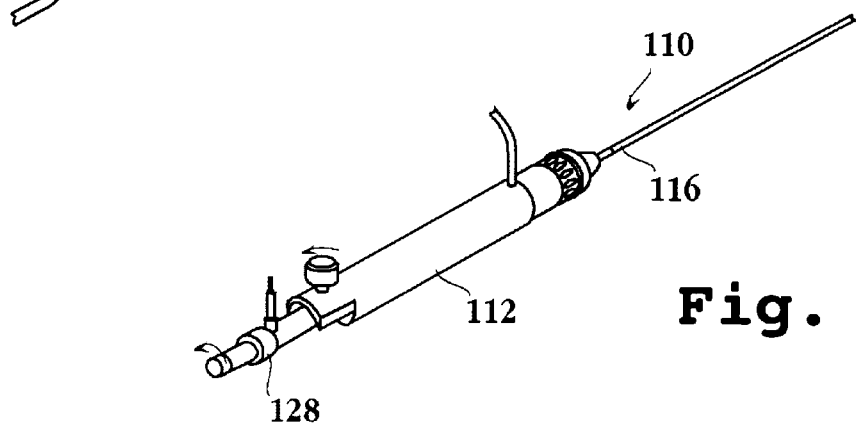
FIG. 27(a) is a perspective view of the RF treatment apparatus of the invention with the introducer removed from the lumen of the electrode.
Figure 27B:
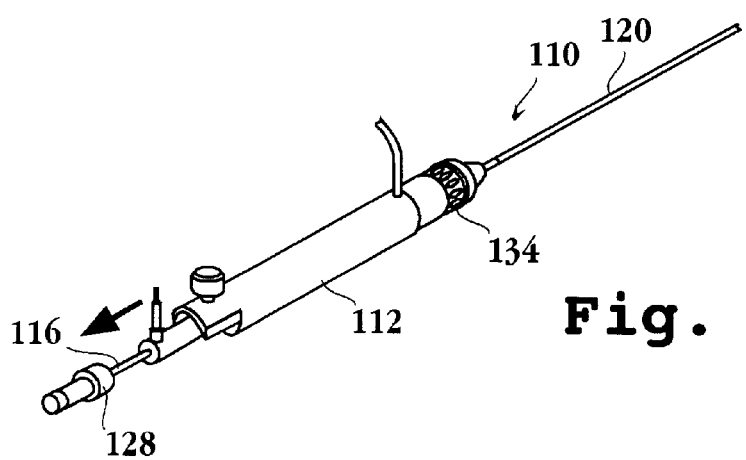
FIG. 27(b) is a perspective view of the apparatus of FIG. 27(a) illustrating the removal of the electrode from the catheter, leaving behind the insulation sleeve.

Referring now to FIG. 27(a), electrode 116 is at least partially positioned in the lumen of catheter 112. Electrode locking cap 128 is mounted at the proximal end of catheter 112, with the proximal end of electrode 116 attaching to electrode locking cap 128. Electrode locking cap 128 is rotated and unlocks from catheter 112. In FIG. 27(*b*), electrode locking cap 128 is then pulled away from the proximal end of catheter 112, pulling with it electrode 116 which is then removed from the lumen of catheter 112. After electrode 116 is removed from catheter 112, insulator sleeve 120 is locked on catheter 112 by insulator retainer cap 134.

Figure 28A:
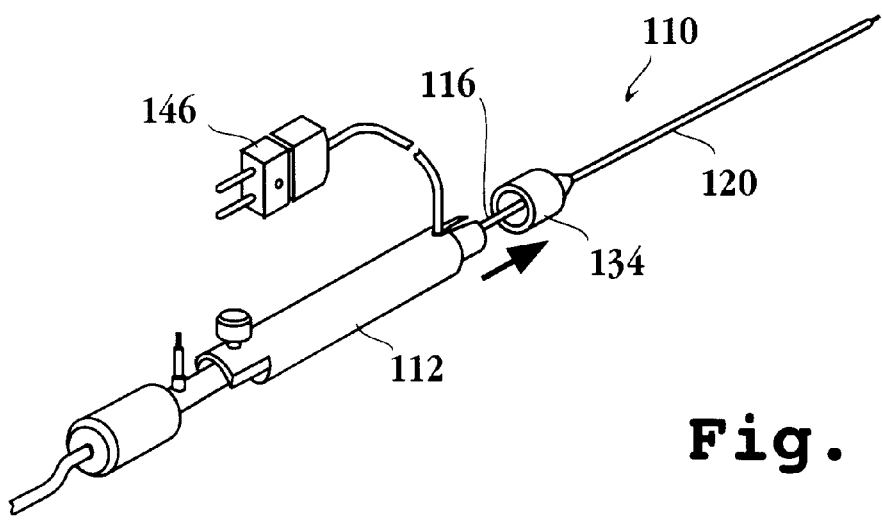
FIG. 28(a) is a perspective view of the RF ablation apparatus of the invention with the insulation sleeve positioned in a surrounding relationship to the electrode which is mounted to the distal end of the catheter.
Figure 28B:
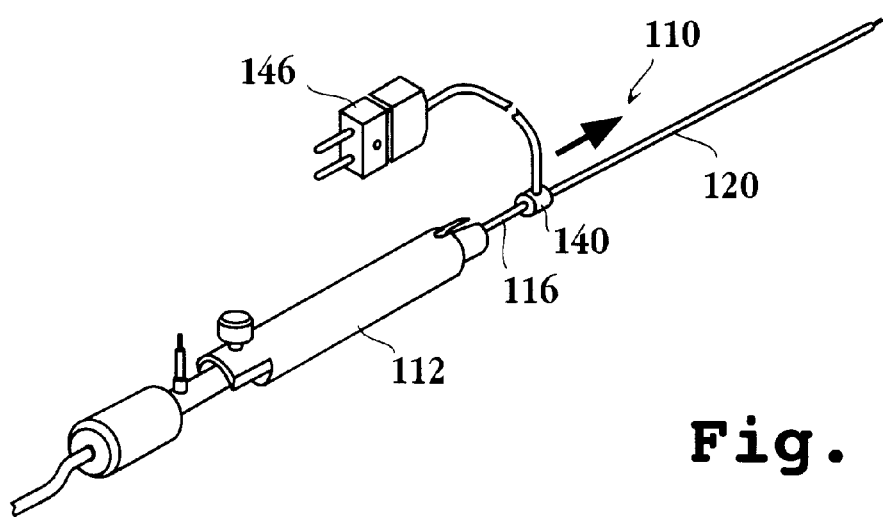
FIG. 28(b) is a perspective view of the RF ablation apparatus of FIG. 28(a) illustrating the removal of the insulation sleeve from the electrode.
Figure 28C:
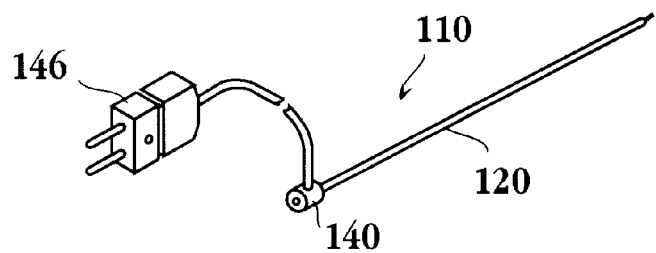
FIG. 28(c) is a perspective view of the insulation sleeve after it is removed from the electrode.

In FIG. 28(*a*), insulator retainer cap 134 is unlocked and removed from catheter 112. As shown in FIG. 28(*b*), insulator sleeve 120 is then slid off of electrode 116. FIG. 28(*c*) illustrates insulator sleeve 120 completely removed from catheter 112 and electrode 116.

Figure 29A:
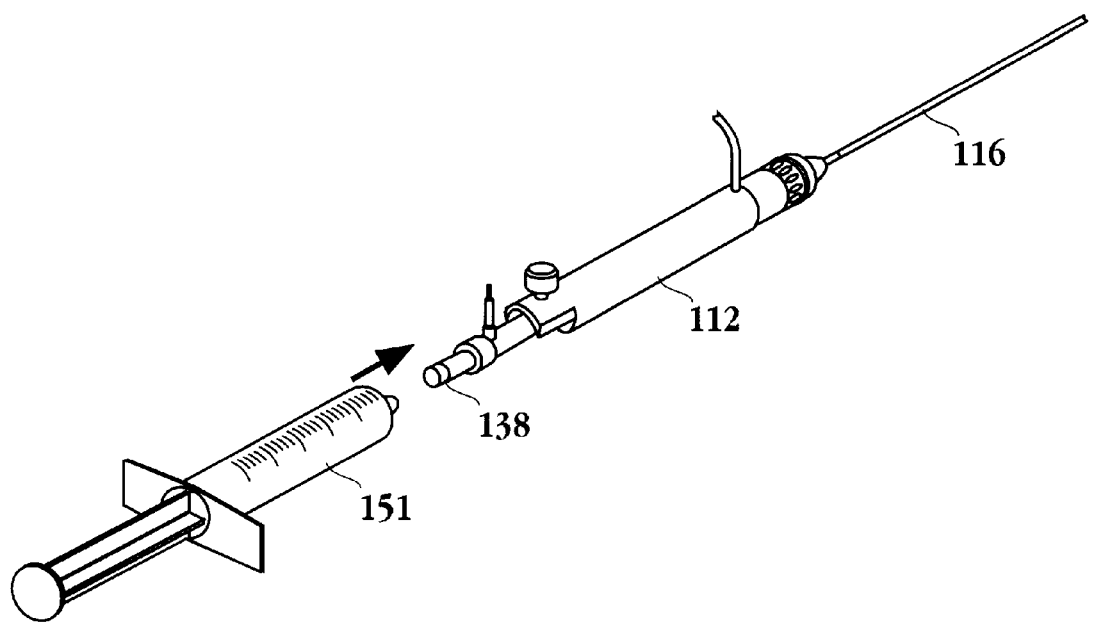
FIG. 29(a) is a perspective view illustrating the attachment of a syringe to the device of FIG. 27(a).
Figure 29B:
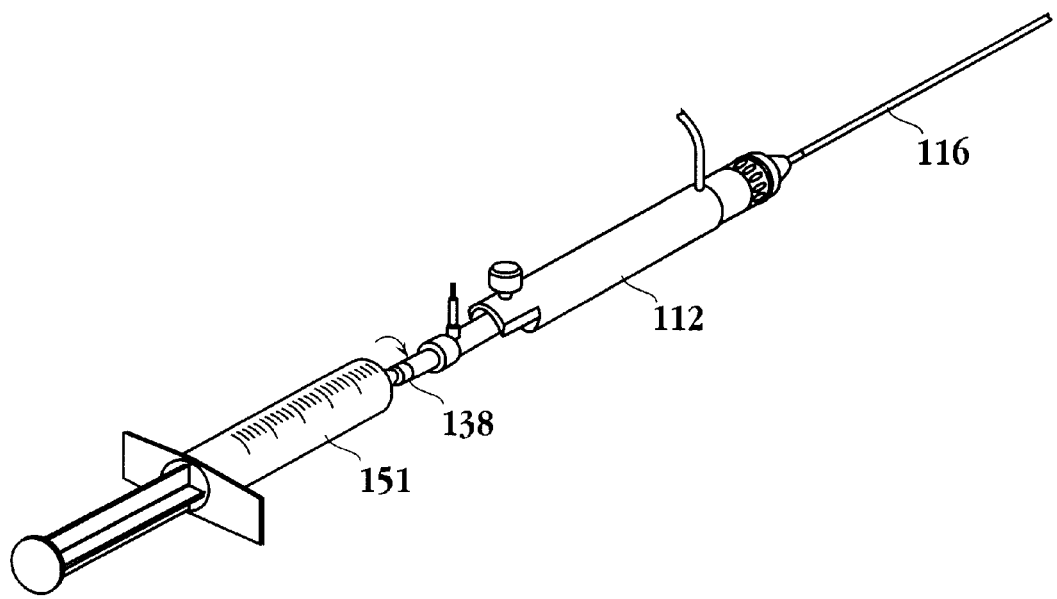
FIG. 29(b) is a perspective view of a syringe, containing a fluid medium such as a chemotherapeutic agent, attached to the RF ablation apparatus of FIG. 27(a).

Referring now to FIGS. 29(*a*) and 29(*b*), after introducer 118 is removed from catheter 112, a fluid source, such as syringe 151, delivering a suitable fluid, including but not limited to a chemotherapeutic agent, attaches to luer connector 138 at the proximal end of catheter 112. Chemotherapeutic agents are then delivered from syringe 151 through electrode 116 to the tumor site. Syringe 151 is then removed from catheter 112 by imparting a rotational movement of syringe 151 and pulling it away from catheter 112. Thereafter, electrode 116 can deliver further RF power to the tumor site. Additionally, electrode 116 and catheter 112 can be removed, leaving only infusion device 150 in the body. Syringe 151 can then be attached directly to infusion device 150 to introduce a chemotherapeutic agent to the tumor site. Alternatively, other fluid delivery devices can be coupled to infusion device 150 in order to have a more sustained supply of chemotherapeutic agents to the tumor site.

Once chemotherapy is completed, electrode 116 and catheter 112 can be introduced through infusion device 150. RF power is then delivered to the tumor site. The process begins again with the subsequent removal of catheter 112 and electrode 116 from infusion device 150. Chemotherapy can then begin. Once it is complete, further RF power can be delivered to the tumor site. This process can be repeated any number of times for an effective multi-modality treatment of the tumor site.

Figure 30:
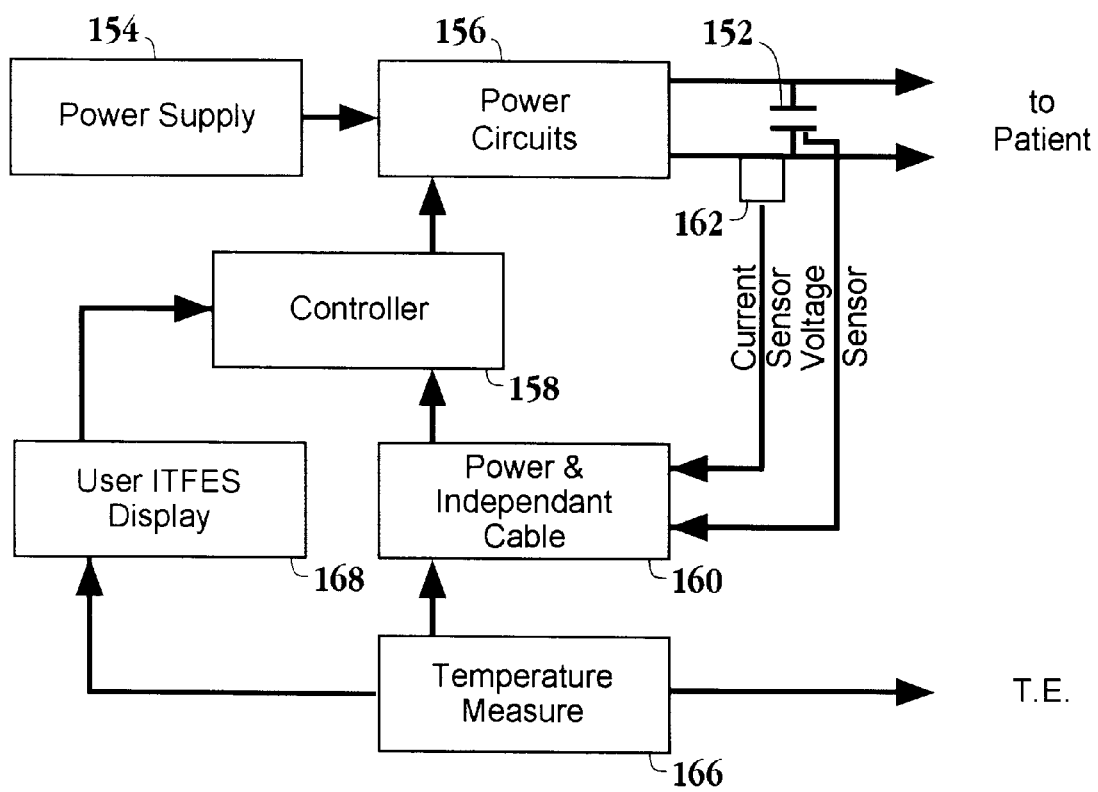
FIG. 30 is a block diagram of an RF treatment system of the invention.

Referring now to FIG. 30, a block diagram of power source 152 is illustrated. Power source 152 includes a power supply 154, power circuits 156, a controller 158, a power and impedance calculation device 160, a current sensor 162, a voltage sensor 164, a temperature measurement device 166 and a user interface and display 168.

Figure 31:
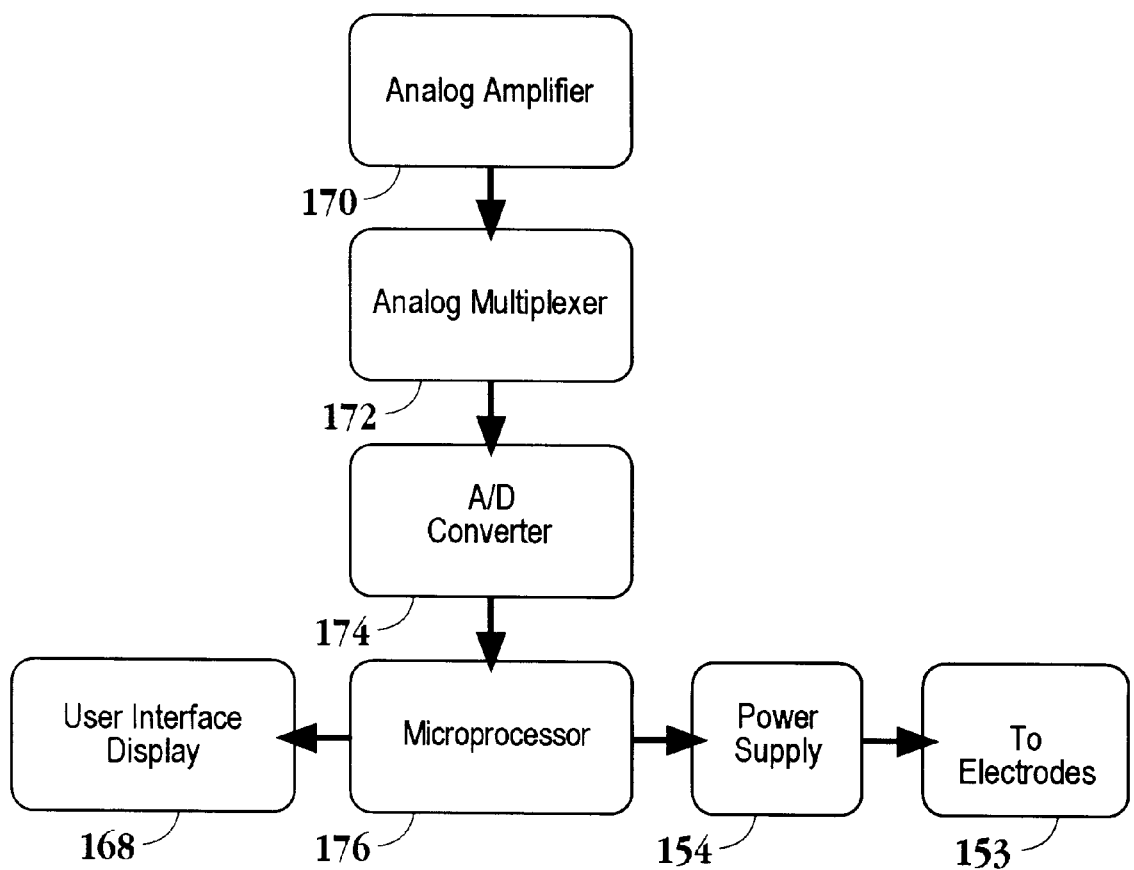
FIG. 31 is a block diagram of an embodiment of the invention which includes a microprocessor.

FIGS. 31(*a*) through 31(*g*) are schematic diagrams of power supply 154, voltage sensor 164, current sensor 162, power computing circuit associated with power and impedance calculation device 160, impedance computing circuit associated with power and impedance calculation device 160, power control circuit of controller 158 and an eight channel temperature measurement circuit of temperature measure device 166, respectively.

Current delivered through each electrode 116 is measured by current sensor 162. Voltage between the electrodes 116 is measured by voltage sensor 164. Impedance and power are then calculated at power and impedance calculation device 160. These values can then be displayed at user interface 168. Signals representative of power and impedance values are received by controller 158.

A control signal is generated by controller 158 that is proportional to the difference between an actual measured value, and a desired value. The control signal is used by power circuits 156 to adjust the power output in an appropriate amount in order to maintain the desired power delivered at the respective electrode 116.

In a similar manner, temperatures detected at thermal sensors 124 and 126 provide feedback for maintaining a selected power. The actual temperatures are measured at temperature measurement device 166, and the temperatures are displayed at user interface 168. Referring now to FIG. 31(*h*), a control signal is generated by controller 159 that is proportional to the difference between an actual measured temperature, and a desired temperature. The control signal is used by power circuits 157 to adjust the power output in an appropriate amount in order to maintain the desired temperature delivered at the respective sensor 124 or 126.

Controller 158 can be a digital or analog controller, or a computer with software. When controller 158 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface 168 includes operator controls and a display. Controller 158 can be coupled to imaging systems, including but not limited to ultrasound, CT scanners and the like.

Current and voltage are used to calculate impedance. Diagnostics can be performed optically, with ultrasound, CT scanning, and the like. Diagnostics are performed either before, during and after treatment.

The output of current sensor 162 and voltage sensor 164 is used by controller 158 to maintain the selected power level at electrodes 116. The amount of RF energy delivered controls the amount of power. A profile of power delivered can be incorporated in controller 158, and a pre-set amount of energy to be delivered can also be profiled.

Circuitry, software and feedback to controller 158 result in process control, and the maintenance of the selected power that is independent of changes in voltage or current, and are used to change, (i) the selected power, including RF, ultrasound and the like, (ii) the duty cycle (on-off and wattage), (iii) bipolar energy delivery and (iv) fluid delivery, including chemotherapeutic agents, flow rate and pressure. These process variables are controlled and varied, while maintaining the desired delivery of power independent of changes in voltage or current, based on temperatures monitored at thermal sensors 124 and 126 at multiple sites.

Controller 158 can be microprocessor controlled. Referring now to FIG. 31, current sensor 162 and voltage sensor 164 are connected to the input of an analog amplifier 170. Analog amplifier 170 can be a conventional differential amplifier circuit for use with thermal sensors 124 and 126. The output of analog amplifier 170 is sequentially connected by an analog multiplexer 172 to the input of analog-to-digital converter 174. The output of analog amplifier 170 is a voltage which represents the respective sensed temperatures. Digitized amplifier output voltages are supplied by analog-to-digital converter 174 to a microprocessor 176. Microprocessor 176 may be a type 68HCII available from Motorola. However, it will be appreciated that any suitable microprocessor or general purpose digital or analog computer can be used to calculate impedance or temperature.

Microprocessor 176 sequentially receives and stores digital representations of impedance and temperature. Each digital value received by microprocessor 176 corresponds to different temperatures and impedances.

Calculated power and impedance values can be indicated on user interface 168. Alternatively, or in addition to the numerical indication of power or impedance, calculated impedance and power values can be compared by microprocessor 176 with power and impedance limits. When the values exceed predetermined power or impedance values, a warning can be given on interface 168, and additionally, the delivery of RF energy can be reduced, modified or interrupted. A control signal from microprocessor 176 can modify the power level supplied by power supply 154.

An imaging system can be used to first define the volume of the tumor or selected mass. Suitable imaging systems include but are not limited to, ultrasound, CT scanning, X-ray film, X-ray fluoroscope, magnetic resonance imaging, electromagnetic imaging and the like. The use of such devices to define a volume of a tissue mass or a tumor is well known to those skilled in the art.

Specifically with ultrasound, an ultrasound transducer transmits ultrasound energy into a region of interest in a patient's body. The ultrasound energy is reflected by different organs and different tissue types. Reflected energy is sensed by the transducer, and the resulting electrical signal is processed to provide an image of the region of interest. In this way, the volume to be ablated is ascertained.

Ultrasound is employed to image the selected mass or tumor. This image is then imported to user interface 168. The placement of electrodes 116 can be marked, and RF energy delivered to the selected site with prior treatment planning. Ultrasound can be used for real time imaging. Tissue characterization of the imaging can be utilized to determine how much of the tissue is heated. This process can be monitored. The amount of RF power delivered is low, and the ablation or hyperthermia of the tissue is slow. Desiccation of tissue between the tissue and each needle 116 is minimized by operating at low power.

Figure 32:
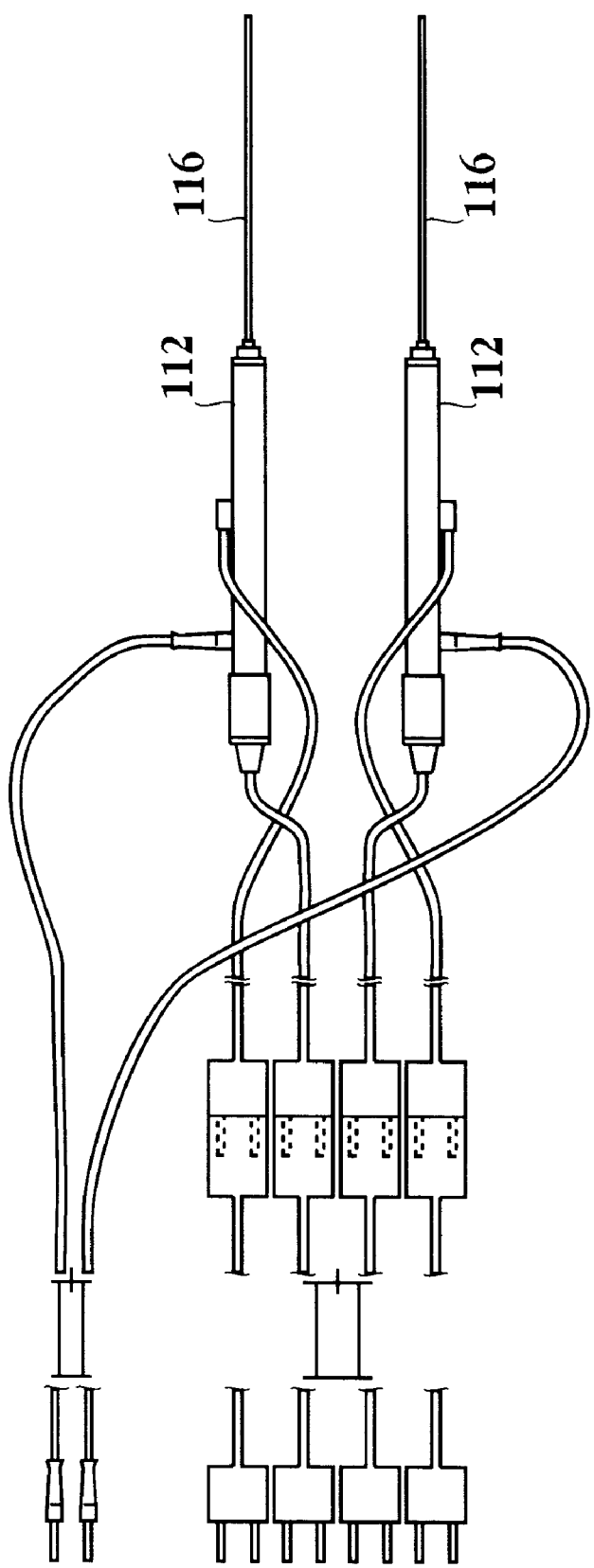
FIG. 32 illustrates the use of two RF treatment apparatus, such as the one illustrated in FIG. 22(a), that are used in a bipolar mode.

The following examples illustrate the use of the invention with two RF treatment apparatus with two electrodes shown in FIG. 32, or a pair of two electrodes, that are used in a bipolar mode to ablate tissue.

EXAMPLE 1

| | |
|---|---|
| Exposed electrode length | 1.5 cm |
| Distance between electrodes | 1.5 cm |
| Power setting | 5 W |
| Ablation time | 10 min. |
| Lesion size | |
| width | 2 cm |
| length | 1.7 cm |
| depth | 1.5 cm |

EXAMPLE 2

| | |
|---|---|
| Exposed electrode length | 1.5 |
| Distance between electrodes | 2.0 |
| Power setting | 7.0 |
| Ablation time | 10 min. |
| Lesion size | |
| width | 2.8 cm |
| length | 2.5 cm |
| depth | 2.2 cm |

EXAMPLE 3

| | |
|---|---|
| Exposed electrode length | 2.5 cm |
| Distance between electrodes | 2.0 cm |
| Power setting | 10 W |
| Ablation time | 10 min |
| Lesion size | |
| width | 3.0 cm |
| length | 2.7 cm |
| depth | 1.7 cm |

EXAMPLE 4

| | |
|---|---|
| Exposed electrode length | 2.5 cm |
| Distance between electrodes | 2.5 cm |
| Power setting | 8 W |
| Ablation time | 10 min. |
| Lesion size | |
| width | 2.8 cm |
| length | 2.7 cm |
| depth | 3.0 cm |

EXAMPLE 5

| | |
|---|---|
| Exposed electrode length | 2.5 cm |
| Distance between electrodes | 2.5 cm |
| Power setting | 8 W |
| Ablation time | 12 min. |
| Lesion size | |
| width | 2.8 cm |
| length | 2.8 cm |
| depth | 2.5 cm |

EXAMPLE 6

| | |
|---|---|
| Exposed electrode length | 2.5 cm |
| Distance between electrodes | 1.5 cm |
| Power setting | 8 W |
| Ablation time | 14 min. |
| Lesion size | |
| width | 3.0 cm |
| length | 3.0 cm |
| depth | 2.0 cm |

EXAMPLE 7

| | |
|---|---|
| With return electrode at 1.5 cm | |
| Exposed electrode length | 2.5 cm |
| Distance between electrodes | 2.5 cm |
| Power setting | 8 W |
| Ablation time | 10 min. |
| Lesion size | |
| width | 3.0 cm |
| length | 3.0 cm |
| depth | 3.0 cm |

EXAMPLE 8

| | |
|---|---|
| Exposed electrode length | 2.5 cm |
| Distance between electrodes | 2.5 cm |
| Power setting | 10 W |
| Ablation time | 12 min. |
| Lesion size | |
| width | 3.5 cm |
| length | 3.0 cm |
| depth | 2.3 cm |

EXAMPLE 9

| | |
|---|---|
| Exposed electrode length | 2.5 cm |
| Distance between electrodes | 2.5 cm |
| Power setting | 11 W |
| Ablation time | 11 min. |
| Lesion size | |
| width | 3.5 cm |
| length | 3.5 cm |
| depth | 2.5 cm |

EXAMPLE 10

| | |
|---|---|
| Exposed electrode length | 3.0 cm |
| Distance between electrodes | 3.0 cm |
| Power setting | 11 W |
| Ablation time | 15 min. |
| Lesion size | |
| width | 4.3 cm |
| length | 3.0 cm |
| depth | 2.2 cm |

EXAMPLE 11

| | |
|---|---|
| Exposed electrode length | 3.0 cm |
| Distance between electrodes | 2.5 cm |
| Power setting | 11 W |
| Ablation time | 11 min. |
| Lesion size | |
| width | 4.0 cm |
| length | 3.0 cm |
| depth | 2.2 cm |

EXAMPLE 12

| | |
|---|---|
| Exposed electrode length | 4.0 cm |
| Distance between electrodes | 2.5 cm |
| Power setting | 11 W |
| Ablation time | 16 min. |
| Lesion size | |
| width | 3.5 cm |
| length | 4.0 cm |
| depth | 2.8 cm |

EXAMPLE 13

| | |
|---|---|
| Two pairs of electrodes (Four electrodes) | |
| Exposed electrode length | 2.5 cm |
| Distance between electrodes | 2.5 cm |
| Power setting | 12 W |
| Ablation time | 16 min. |
| Lesion size | |
| width | 3.5 cm |
| length | 3.0 cm |
| depth | 4.5 cm |

EXAMPLE 14

| | |
|---|---|
| Two pairs of electrodes (Four electrodes) | |
| Exposed electrode length | 2.5 cm |
| Distance between electrodes | 2.5 cm |
| Power setting | 15 W |
| Ablation time | 14 min. |
| Lesion size | |
| width | 4.0 cm |
| length | 3.0 cm |
| depth | 5.0 cm |

The foregoing description of preferred embodiments of the present invention has been provided for the purposes of illustration and description. It is not intended to be exhaustive or to limit the invention to the precise forms disclosed. Obviously, many modifications, variations and different combinations of embodiments will be apparent to practitioners skilled in this art. Also it will be apparent to the skilled practitioner that elements from one embodiment can be recombined with one or more other embodiments. It is intended that the scope of the invention be defined by the following claims and their equivalents.

What is claimed is:

1. A cell necrosis apparatus, comprising:

an elongated delivery device including a lumen;

an energy delivery device including at least a first and a second RF electrode each with a tissue piercing distal portion, the first and second RF electrodes being positionable in the elongated delivery device in a compacted state and being preformed to assume a curved shape when deployed, the first and second RF electrodes exhibiting a changing direction of travel when advanced from the elongated delivery device to a selected tissue site;

at least one of the elongated delivery device, or at least one of the first or second RF electrodes having an infusion lumen terminating in at least one infusion port for fluid delivery therethrough;

a source of RF power operatively connected to the energy delivery device for supplying RF power thereto, to ablate tissue at the tissue site, and a measurement device operatively connected to the energy delivery device and to the RF power source for measuring at least one of the current or voltage at the tissue site.

2. The apparatus of claim 1, wherein the measurement device is operable to control the delivery of power from the RF source to the energy delivery device at the tissue site.

3. The apparatus of claim 1, further comprising a sensor coupled to at least one of said RF electrodes.

4. The apparatus of claim 1, wherein the first RF electrode includes a first infusion lumen and the second RF electrode includes a second infusion lumen, and the apparatus further includes a liquid reservoir operatively connected to at least one of said infusion lumens for supplying a fluidic medium under pressure through the infusion lumen into said tissue site.

5. The apparatus of claim 4, wherein the first infusion lumen terminates at a first infusion port to define a first fluid path and the second infusion lumen terminates at a second infusion port to define a second fluid path.

6. The apparatus of claim 5, wherein the first and second fluid paths are configured to be one of fluidically or electrically isolated from each other.

7. The apparatus of claim 5, wherein the first and second fluid flow paths are configured to have a fluid flow rate to first RF electrode be independent of a fluid flow rate to the second RF electrode.

8. The apparatus of claim 4, wherein the energy delivery device is configured to deliver energy to the tissue site and to infuse a delivered fluid into a selected portion of the tissue site.

9. The apparatus of claim 4, wherein said reservoir contains the fluidic medium and is operable to infuse said medium under pressure through said infusion lumen, and wherein at least one of the infusion port or the energy delivery device is adapted to deliver a fluidic medium.

10. The apparatus of claim 9, wherein the fluidic medium is one of a paste, a gel or an emulsion.

11. The apparatus of claim 9, wherein the fluidic medium has sufficient viscosity to substantially remain at the tissue site.

12. The apparatus of claim 9, wherein the fluidic medium has sufficient viscosity to substantially remain at the tissue site under hyperthermic conditions.

13. The apparatus of claim 9, wherein the conductive fluidic medium includes one of an aqueous solution, an electrolytic solution or a saline solution.

14. The apparatus of claim 4, wherein the apparatus further includes a first liquid reservoir operatively connected to the first RF electrode infusion lumen for supplying a first fluidic medium under pressure through the first infusion lumen into said tissue site and a second liquid reservoir operatively connected to the second RF electrode infusion lumen for supplying a second fluidic medium under pressure through the second infusion lumen into said tissue site.

15. The apparatus of claim 4, wherein the first fluidic medium is a conductive solution and the second fluidic medium is a chemotherapeutic agent.

16. The apparatus of claim 9, wherein the apparatus is configured to control the delivery of the fluidic medium.

* * * * *